US007041484B1

(12) United States Patent
Baga et al.

(10) Patent No.: US 7,041,484 B1
(45) Date of Patent: May 9, 2006

(54) STARCH BRANCHING ENZYMES

(75) Inventors: Monica Baga, Saskatoon (CA);
Mingsheng Peng, Saskatoon (CA);
Ramesh B. Nair, Saskatoon (CA);
Anne Repellin, Saskatoon (CA); Ming Gao, Saskatoon (CA); Pierre Hucl, Saskatoon (CA); Graham J. Scoles, Saskatoon (CA); Ravindra N. Chibbar, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 458 days.

(21) Appl. No.: 10/110,777

(22) PCT Filed: Oct. 27, 2000

(86) PCT No.: PCT/CA00/01276

§ 371 (c)(1),
(2), (4) Date: Aug. 8, 2002

(87) PCT Pub. No.: WO01/32886

PCT Pub. Date: May 10, 2001

Related U.S. Application Data

(60) Provisional application No. 60/162,144, filed on Oct. 29, 1999.

(51) Int. Cl.
*C12N 15/82* (2006.01)
*C12N 15/29* (2006.01)
*C12N 5/10* (2006.01)
*C12P 19/04* (2006.01)
*A01H 5/00* (2006.01)

(52) U.S. Cl. ............ 435/97; 435/320.1; 435/193; 435/69.1; 435/419; 800/284; 800/278; 800/286; 800/320.3; 536/23.6; 536/24.5; 536/23.2

(58) Field of Classification Search .......... 435/97, 435/419, 69.1, 320.1, 193; 536/23.6, 24.5, 536/23.2; 800/284, 278, 286, 320.3
See application file for complete search history.

(56) References Cited

U.S. PATENT DOCUMENTS 6,730,825 B1 * 5/2004 Goldsbrough et al. ...... 800/284

FOREIGN PATENT DOCUMENTS

WO WO 94 09144 A 4/1994
WO WO 97 22703 A 6/1997
WO WO 98 14601 A 4/1998
WO WO 99 14314 A 3/1999

OTHER PUBLICATIONS

Rahman et al. (1997), (A complex arrangement genes at a starch branching enzyme I locus in the D-genome of wheat, Genome 40 (4), 465-474).*
Repellin et al. (1997) (Isolation of Starch branching enzyme I cDNA from a wheat endosperm library (accession No. Y12320), Plant physiology 114:1145-1145).*
Baga, Monica et al: "*Isolation of a cDNA encoding a granule-bound 152-kilodalton starch-branching enzyme in wheat.*" Plant Physiology (Rockville), vol. 124, No. 1, Sep. 2000, pp. 253-263, XP002172352, ISSN: 0032-0889.
Peng, Minsheng et al.: "*Starch-branching enzymes preferentially associated with A-type starch granules in wheat endosperm.*" Plant Physiology (Rockville), vol. 124, No. 1, Sep. 2000, pp. 265-272, XP002172353, ISSN: 0032-0889.
Database EMBL 'Online!' Accession No.: Y12320, Apr. 9, 1997, Repellin, A., et al.: "*T.aestivum mRNA for starch branching enzyme I*" XP002172358.
Repellin, A., et al.: "*Isolation of a Starch Branching Enzyme I cDNA from a Wheat Endosperm library* (Accession No. Y12320) (PGR97-094)", Plant Gene Register PGR97-094 Plant Physiol. 114:1135, 1997, XP002172354.
Database EMBL 'Online!' Accession No: AF002820, Jul. 3, 1997, Rahman S., et al.; "*Triticum aestivum starch branching enzyme I (wSBE 1-D2) mRNA, complete cds.*" XP002172359.
Database EMBL 'Online!' Accession No.: AF076679, May 14, 1999, Rahman S., et al.; "*Triticum aestivum starch branching enzyme-I (SBE-I) mRNA, complete cds.*" XP002172360.
Rahman S., et al.: "*Characterisation of a gene encoding wheat endosperm branching enzyme-I*", Theor. Appl. Genet., vol. 98, 1999, pp. 156-163, XP001010371.

(Continued)

*Primary Examiner*—Rebecca E. Prouty
*Assistant Examiner*—Kagnew Gebreyesus

(57) ABSTRACT

The invention provides a novel starch branching enzyme that is bound to A-type starch granules in wheat, barley, rye or triticale. The enzyme is not substantially associated with B-type starch granules. A cDNA sequence encoding an isoform of the enzyme has been isolated from the wheat cultivar Fielder and deduced amino acid sequence has been determined.

3 Claims, 13 Drawing Sheets

OTHER PUBLICATIONS

Baga, Monica et al.; "*A starch-branchng enzyme gene in wheat produces alternatively spliced transcripts.*" Plant Molecular Biology, vol. 40, No. 6, Aug. 1999, pp. 1019-1030. XP002172355, ISSN: 0167-4412.

Schofield, J. D. et al.: "*Wheat Starch Granule Proteins and Their Technological Significance*". 89573-523-7, 1987, pp. 407-420, XP001014172, Bournemouth, England, UK, 1986, VII+523P. Ellis Horwood Ltd.: Chichester, England, UK (Dist By VCH Verlagsgesellschaft: Weinheim, West Germany; VCH Publishers: New York, New York, U.S.A.), Illus. ISBM 0-89573-523-7, 1987.

Takaoka Motoko et al.: "*Structural characterization of high molecular weight starch granule-bound proteins in wheat (Triticum aestivium L.).*" Journal of Agricultural and Food Chemistry, vol. 45, No. 8, 1997, pp. 2929-2934, XP002172356, ISSN: 0021-8561.

Rahman, Sadequr et al.: "*The major proteins of wheat endosperm starch granules.*" Australian Journal of Plant Physiology, vol. 22, No. 5, 1995, pp. 793-803, XP002043127, ISSN: 0310-7841.

Mu-Forster C. et al.: "Physical Association of Starch Biosynthetic Enzymes With Starch Granules of Maize Endosperm", Plant Physiology, US, American Society of Plant Physiologists, Rockville, MD, vol. 111, 1996, pp. 821-829, XP002056414, ISSN: 0032-0889.

Baga, Monica et al: "*Wheat Starch Modification Through Biotechnology*" Starch Starke, DE, Wiley-VCH Verlag, Weinheim, vol. 51, No. 4, Apr. 1999, pp. 111-116, XP000828602, ISSN:0038-9056.

* cited by examiner

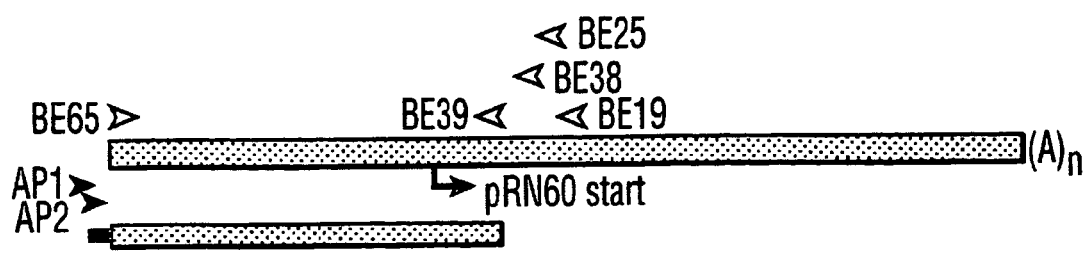
FIG. 3A
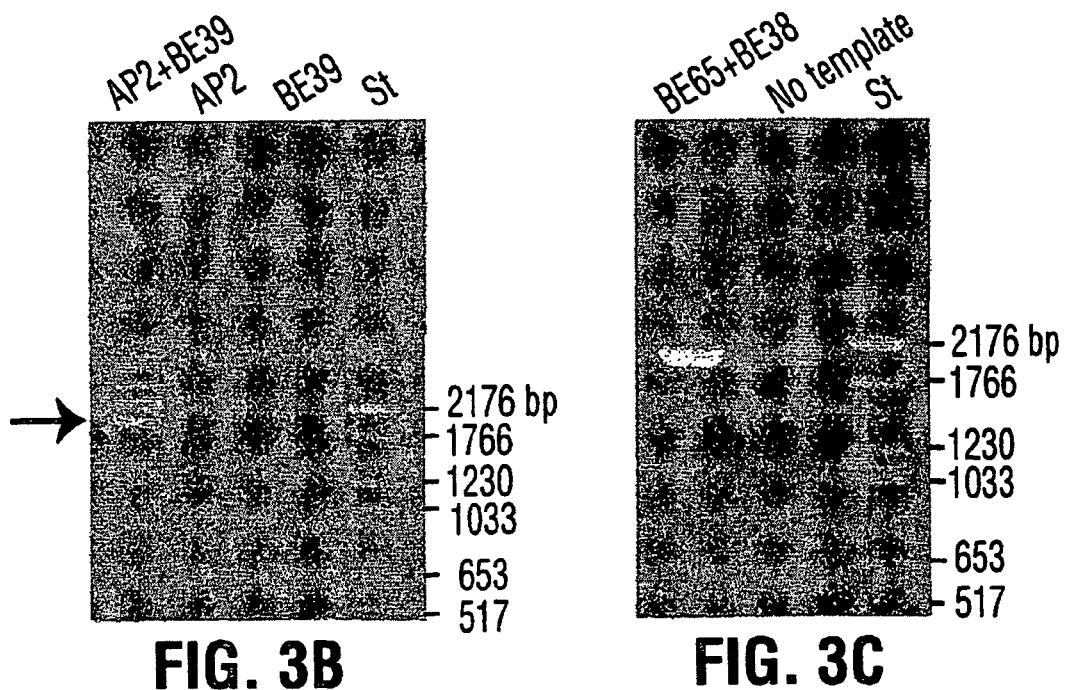
FIG. 3B  FIG. 3C

FIG. 4A

*[Figure 4A shows a DNA and protein sequence alignment with annotations including labels BE65, BE63, BE39, BE38, BE25, BE12, and "pRN60 start". Sequence positions run from 150 to 2250 on the right side, with corresponding amino acid position numbers 12 through 662.]*

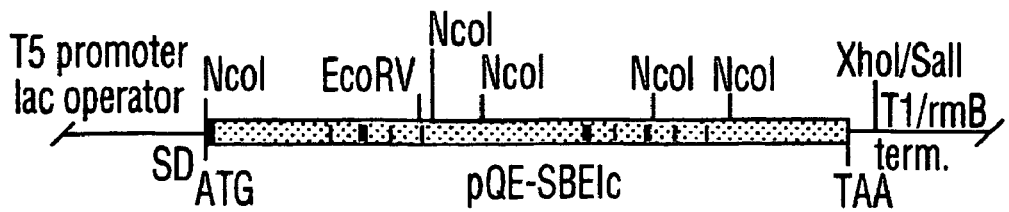
FIG. 6A
| Strain/plasmids | Iodine staining | BE activity |
|---|---|---|
| DH5α / pREP4-cm pQE30 | Yellow / brown | 0.2 +/- 0.1 |
| KV832/ pREP4-cm pQE30 | Blue /grey | <0.01 |
| KV832/ pREP4-cm pQE-SBEIc | Brown | 0.9 +/- 0.3 |
FIG. 6B
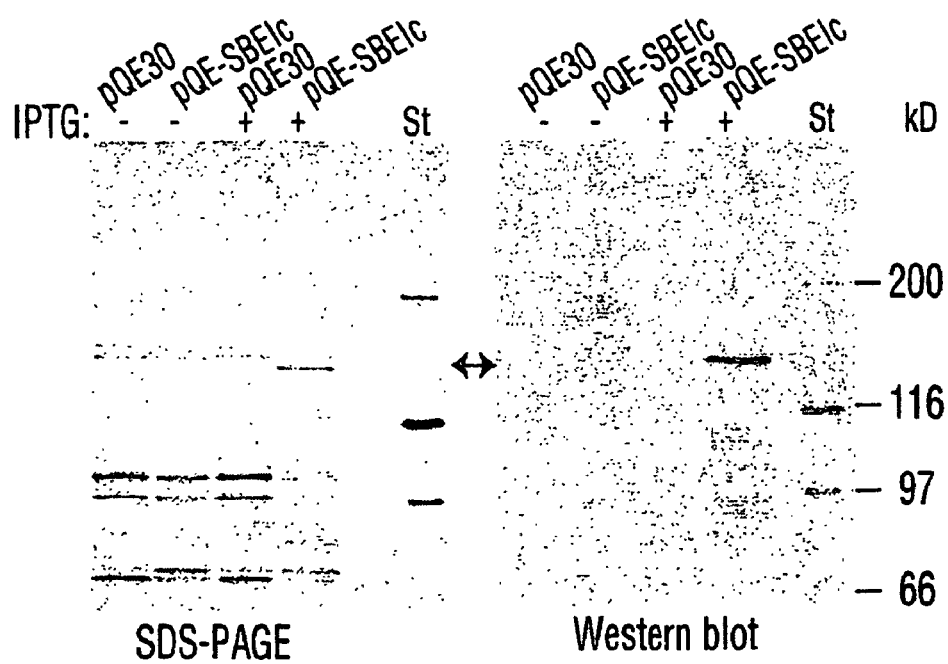
FIG. 6C

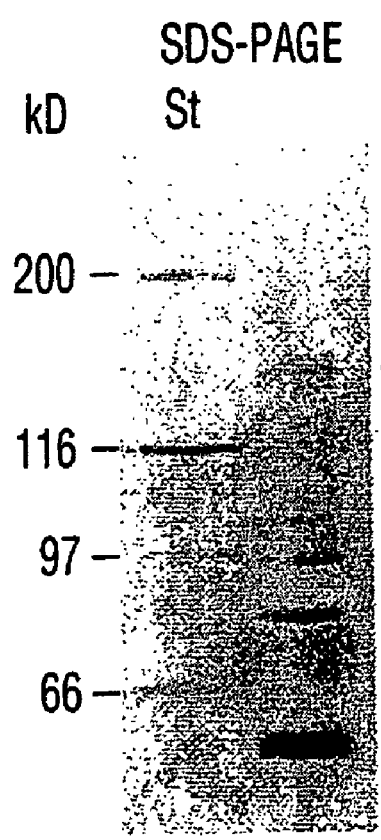
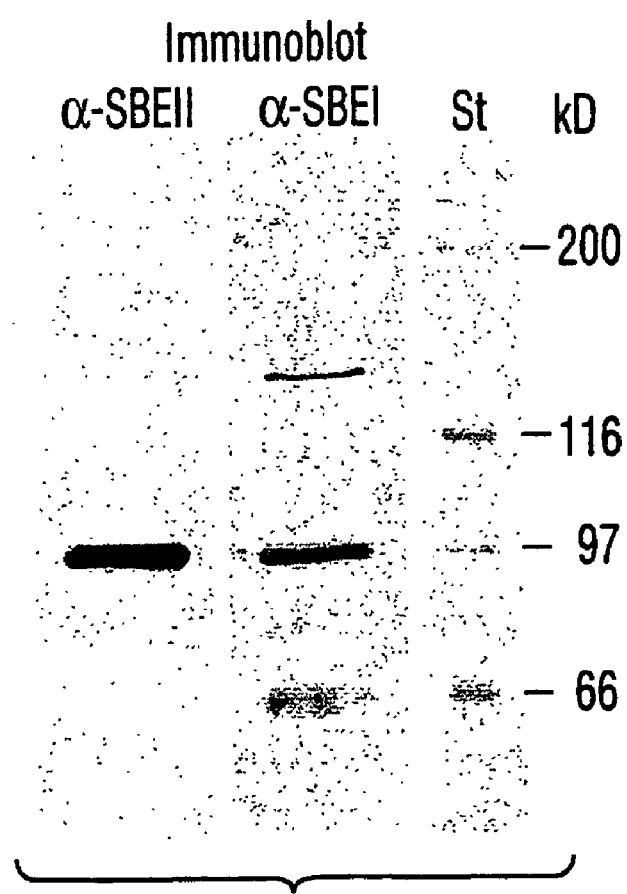
FIG. 7A     FIG. 7B

SEQUENCE LISTING

<110> National Research Council of Canada

<120> Starch Branching Enzymes

<130> 45187pt

<140>
<141>

<150> US60/162,144
<151> 1999-10-29

<160> 2

<170> PatentIn Ver. 2.1

<210> 1
<211> 4563
<212> DNA
<213> Triticum aestivum

<400> 1
```
gggactttcg tccgccacca aggctgacag ctccaccgcc ctcggttgcg ccgtcgacga   60
cgatgctttg cctcagctcc tctctcctgc cgcgcccgtc tgccgctgct gaccggccgg  120
ctcccgggat catcgcgggc ggcggcggca agcggctgag cgtggtgccg gctgtcccgt  180
ttttacttcg ctggtcgtgg ccacggaagg ccaagagcag gtcttctgtt tccgtgactg  240
cacgaggaaa caaaattgcg gcagcaaatg gatatggttc tgaccacctt cccatgtatg  300
atctggaacc aaagttggct gaattcaaag accacttcaa ctatacgatg aaaaggtacc  360
ttgaacagaa acttttgatt gagaaacatg agggaggcct agaggaattc tctaaaggct  420
atttgaagtt tgggatcaac acggagcatg gtgcatctct gtacagggaa tgggcccctg  480
cagcagagga agcacaacta gttggtgact tcaacaactg gaatggttct ggccacaaga  540
tgacgaagga taactttggc gtttggtcaa tcaggatttc ccatgtcaat gggaaacctg  600
ccatccctca caattccaag gttaaatttc gatttaggca tgatggagta tgggttgaac  660
ggattccagc atggattcgt tatgcaactg ttactgcctc tgaatctgga gctccatatg  720
atggtgttca ctgggatcca ccaactagtg aaaggtatgt atttaaccat cctcgacctc  780
caaagcctga tgttccacgt atctatgagg ctcatgtggg ggtgagtggt ggaaagcttg  840
aagcaggcac acacagggaa tttgcagaca atgtgttacc gcgcttaagg caactacat   900
acaacacggt tcagttgatg ggaatcatgg aacattctga cgctgcttct tttgggtatt  960
atgtgacgaa tttcttcgca gttagcagca gatcaggcac accagacgac ctcaaatatc 1020
ttattgacaa ggcacatagt cttggattgt gtgttctgat ggatgttgtc cacagccatg 1080
cgagcaataa tgtgatagat ggtcccaatg gctatgatgt tggacaaagt gcacacgaat 1140
cctatttcta cacaggagac agggctata ataagatgtg gaatggccgc atgttcaact 1200
atgccaattg ggaggtccta agattcctgc tttccaattt gagatattgg atggacgaat 1260
tcatgtttga tggcttccga tttgttgggg ttacatcgat gctatataat caaaatggta 1320
tcaatatgtc attcactgga aattacaaag agtatttgg tttggatacc aatgtagatg 1380
cagttgttta tatgatgctc gcgaaccatt taatgcacaa actctaccca gaagcaattg 1440
ttgtggccgt agatgtttca ggcatgccag ttctttgttg gccagttgat gaaggtggat 1500
tagggtttga ctatcgccag gctatgacta ttcccgatag atggattgaa tacttggaga 1560
acaaaggtga tcaacagtgg tcaatgagta gtgtaatatc acaaactttg actaacaggc 1620
gatatccgga aaagttcatt gcgtatgctg agaggcaaaa tcattctatt attggcagca 1680
agactatggc atttctcttg atgggatggg aaacgtattc cggtatgtcg gccatggagc 1740
ctgattcacc tacaatagat cgtggcattg cacttcaaaa gatgattcat ttcatcagga 1800
tggcctttgg aggtgatagc tacttaaaat ttatgggtaa tgagtacatg aatgcatttg 1860
atcaagcagt ggacacgccc agcgataaat gttccttcct atcatcatca aagcagactg 1920
ccagcgacat gaatgaggaa gaaaaggcca agagcaagtt ctctgttccc gtgtctgcgc 1980
caagagacta caccatggca acagctgaag atggtgttgg cgaccttccg atatacgatc 2040
```

STARCH BRANCHING ENZYMES

CROSS-REFERENCE TO RELATED APPLICATION

This application is the National Phase of International (PCT) Application Ser. No. PCT/CA00/01276 filed Oct. 27, 2000 and claims the priority right of Provisional Application Ser. No. 60/162,144 filed Oct. 29, 1999 by Applicants herein.

TECHNICAL FIELD

The invention relates to the field of plant molecular biology, particularly to enzymes of starch bio-synthesis.

BACKGROUND ART

The endosperm of wheat, barley, rye and triticale contain large A-type and small B-type starch granules at maturity[1]. In wheat, the large A-type starch granules are more than 10 μm in diameter and lenticular in shape, while B-type starch granules are less than 10 μm in diameter and roughly spherical in shape[2]. Because A- and B-type starch granules have significantly different chemical compositions and functional properties[3], wheat cultivars with predominantly A- or B-type starch granules would be very useful to the food and non-food industries.

A-type starch granules are produced in amyloplast at about four to five days-post-anthesis (DPA), and their number increases until 12 to 14 DPA[4]. Subsequently, the A-type starch granules grow in size to an eventual diameter of from 10 μm to more than 36 μm. The number of A-type starch granules per endosperm is constant from about 15 DPA to maturity.

B-type starch granules are actively initiated about 14–16 DPA. Both the number and size of B-type starch granules increase until wheat grain matures. The diameter of B-type starch granules is less than 10 μm[2]. The mechanisms controlling the initiation and size growth of A- and B-type starch granules are unknown. Based on the current knowledge about starch granule synthesis, several mechanisms could be proposed. The initiation and size growth of A- and B-type starch granules may be controlled by different isoforms of starch synthases (SS), starch branching enzymes (SBE), and debranching enzymes (DBE). These enzymes are involved in the biogenesis of plant starch granules[5]. In the barley shrunken endosperm mutant (shx), the size of A-type starch granules is reduced, giving the appearance of a unimodal size distributions. The soluble starch synthase I (SSS I) activity in the shx endosperm is 86% lower relative to the wild type, suggesting that SSS-I may play a role in controlling the size growth of A-type starch granules[7]. However, there are no experimental results showing genetic control of starch granule size distribution in wheat[8, 9].

Starch branching enzyme (α-1,4-glucan-6-glycosyltransferase; EC 2.4.1.18, SBE) is a key enzyme in the starch biosynthesis pathway. The enzyme acts on glucose polymers and catalyses excision and transfer of glucan chains to the same or other glucan molecules. Translocated chains are attached to the polymer through α-1,6-glucosidic bonds to form branches on the α-1,4-linked glucose backbone. All of the reported SBE from plants to date can be divided into two classes, SBEI and SBEII, based on their amino acid sequences[10]. Most of the characterised plant SBEs are in the 80–100 kDa molecular mass range and, like all enzymes of the α-amylase family, carry a $(\beta\alpha)_8$ barrel domain with four highly conserved regions at the active site[11]. Analysis of plants with reduced SBEII activity and enzyme assays performed with purified SBEI and SBEII proteins suggest that the two enzyme classes differ in their enzymatic specificity[12, 13]. The biochemical data suggest that SBEI favours transfer of long glucan chains and acts primarily on amylose, whereas SBEII produces shorter branches and prefers amylopectin as substrate[14, 15, 16]. However, the exact role of the different SBE classes in the formation of the branched glucan polymers in planta is not clear. There is no previous evidence to suggest that there are SBEs specific to A- or B-type starch granules.

DISCLOSURE OF THE INVENTION

In a first aspect, the invention provides a starch branching enzyme that is bound to A-type starch granules in wheat, rye, barley or triticale endosperm.

In a second aspect, the invention provides a DNA sequence encoding one of the starch branching enzymes that is bound to A-type starch granules in wheat, rye, barley or triticale endosperm.

In a third aspect, the invention provides a method for increasing the concentration of A-type starch granules in endosperm of a wheat, rye, barley or triticale plant by over-expressing in the plant a gene encoding a starch branching enzyme that is bound to A-type starch granules.

In a fourth aspect, the invention provides a method for decreasing the concentration of A-type starch granules in endosperm of a wheat, rye, barley or triticale plant by suppressing the activity of a starch branching enzyme that is bound to A-type starch granules.

In a fifth aspect, the invention provides a method for decreasing the concentration of A-type starch granules in endosperm of a wheat, rye, barley or triticale plant by suppressing the transcription and/or translation of a gene encoding a starch branching enzyme that is bound to A-type starch granules in wheat, rye, barley or triticale endosperm.

In a sixth aspect, the invention provides a method of modifying starch granule morphology in a plant expressing a gene encoding a starch branching enzyme that is bound to A-type starch granules in wheat, rye, barley or triticale endosperm.

In a seventh aspect, the invention provides a method for analysing a plant to determine the presence or absence of DNA encoding granule bound starch branching enzyme, comprising the steps of:
  providing a probe capable of hybridising with a DNA encoding a starch branching enzyme that is bound to A-type starch granules in wheat, rye, barley or triticale endosperm;
  exposing the probe to sequences of DNA derived from the genome of the plant; and
  detecting whether hybridisation with the probe has occurred.

In an eight aspect, the invention provides a method for analysing a plant to determine the presence or absence of transcripts encoding granule bound starch branching enzyme, comprising the steps of:
  providing a probe capable of hybridising with mRNA encoding a starch branching enzyme that is bound to A-type starch granules in wheat, rye, barley or triticale endosperm;
  exposing the probe to RNA prepared from the plant or used in in situ hybridisation analysis, and detecting whether hybridisation with the probe has occurred;

providing specific primer for detection of transcripts encoding a granule bound starch branching enzyme in wheat; where detection is accomplished by RT-PCR analysis.

In a ninth aspect the invention provides an antibody raised to a starch branching enzyme that is bound to A-type starch granules in wheat, rye, barley or triticale endosperm.

In a tenth aspect, the invention provides a method for analysing a plant to determine the presence or absence of granule bound starch branching enzyme, comprising the steps of:

exposing the proteins of the plant to an antibody raised to a starch branching enzyme that is bound to A-type starch granules in wheat, rye, barley or triticale endosperm; and detecting whether the antibody has bound a starch branching enzyme that is bound to A-type starch granules in wheat, rye, barley or triticale endosperm.

The invention also relates to a method of genetically transforming a plant so that the plant expresses a starch branching enzyme that is bound to A-type starch granules in wheat, barley, or triticale endosperm.

The invention further relates to a genetically modified plant expressing a starch branching enzyme that is bound to A-type starch granules in wheat, barley, or triticale endosperm.

The invention also relates to a genetically modified plant having within its genome a hybrid gene, wherein the hybrid gene comprises a DNA sequence encoding a starch branching enzyme that is bound to A-type starch granules in wheat, barley or triticale endosperm, or a fragment thereof, fused to a passenger-gene.

DETAILED DESCRIPTION OF THE INVENTION

A Analysis of total RNA (20 μg) prepared from developing kernels harvested at different DPA. The blot was hybridised with probe 2 (FIG. 1) and estimated sizes of hybridising RNA species are shown to the left. Migration of RNA size markers is indicated to the right.

B Same blot as above hybridised with a 25S rRNA DNA probe.

FIG. 3 shows isolation of cDNA corresponding to the 5' end of the 4.6 kb Sbe1c transcript.

A Schematic illustration of the 4.6 kb Sbe1c transcript and product obtained from 5'-RACE analysis. Start of pRN60 sequence and location of PCR primers used in the 5'-RACE and RT-PCR reactions are indicated.

B Gel analysis of 5'-RACE products obtained in reactions with primers indicated and poly(A)+ RNA prepared from 12-day-old wheat kernels. Arrows indicate migration of product carrying the 5' end of the 4.6 kb Sbe1c cDNA. Migration of standard DNA fragments are indicated to the right.

C Gel analysis of RT-PCR products obtained from reactions with PCR primers BE65 and BE38.

Figure 4B:
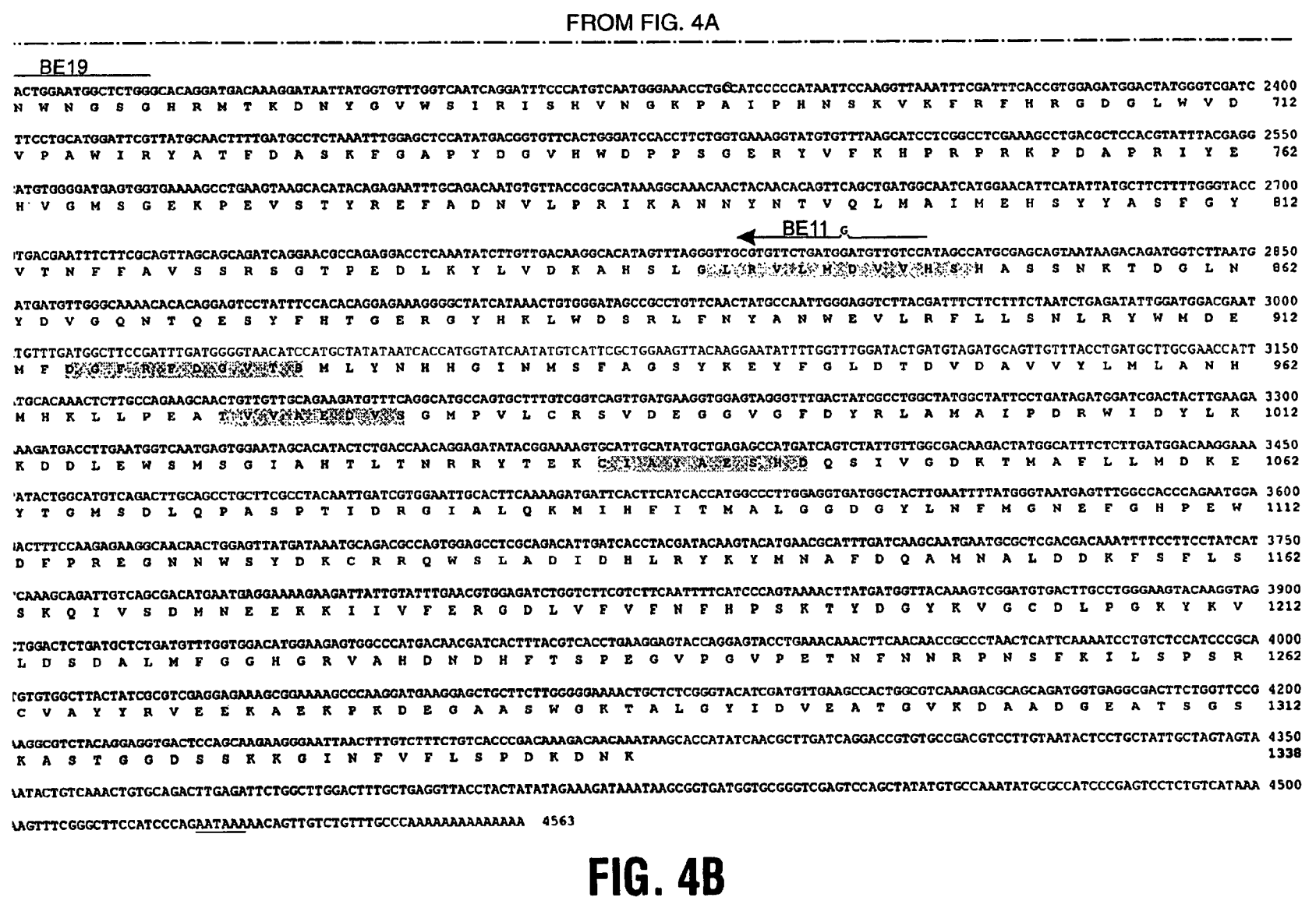

FIG. 4 shows the nucleotide sequence and deduced amino acid sequence of the 4.6 kb SBEIc transcript produced in the wheat endosperm. Possible polyadenylation sequence is underlined and proposed transit peptide cleavage site is indicated by an vertical arrow. Shadowed regions represent conserved sequences in enzymes belonging to the α-amylase family[11]. Start of pRN60 sequence and location of PCR primers used in the study are indicated.

Figure 5:
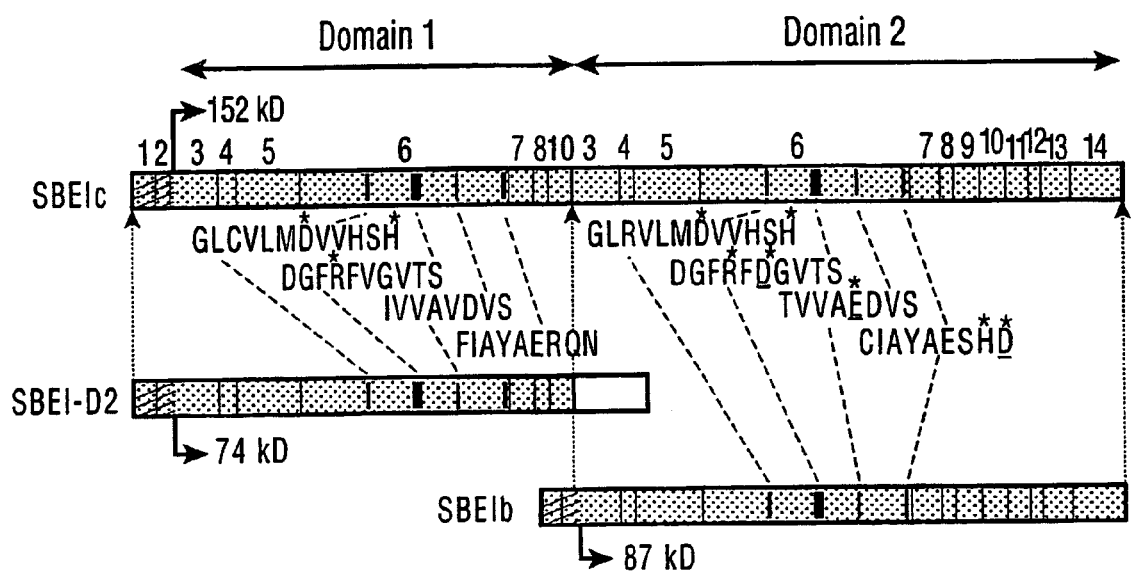

FIG. 5 shows a schematic illustration of SBEIc precursor encoded by 4.6 kb Sbe1c transcript. DNA sequences corresponding to exons 1 to 14 on wheat genomic Sbe1[17] are indicated. Hatched areas indicate location of predicted transit peptide and domains 1 and 2 encompass SBEI-like sequences. The location of the four highly conserved regions on $(\beta\alpha)_8$ barrels of amylolytic enzymes[11] are indicated by black boxes and their sequences are shown below. Highly conserved residues are indicated by asterisks and catalytic residues present only on domain 2 are underlined. SBEIc is aligned with the SBEI-like protein deduced from the wSBEI-D2 cDNA[18] and the wheat 87 kD SBEIb[19].

FIG. 6 shows the expression analysis of Sbe1c in *Escherichia coli*.

A Schematic illustration of the expression vector pQE-SBEIc carrying sequences encoding mature SBEIc with histidine tag (black box) added at the amino-terminal end.

B Analysis of BE activity by iodine staining and phosphorylase α stimulation assay. BE activities were determined from the BE-positive strain DH5α and the BE-deficient strain KV832, transformed with plasmids indicated. Construct pREP4-cm expresses the Lac repressor and pQE30 is a cloning vector used for construction of pQE-SBEIc. The BE activity values and standard errors determined by the phosphorylase α stimulation assay[20] are expressed as μmol glucose-1-phosphate incorporated mg protein$^{-1}$ min$^{-1}$ and were determined from three separate experiments.

C SDS-PAGE and immunoblot analysis of recombinant wheat SBEIc produced in *Escherichia coli*. Total cell extracts of non-induced and IPTG-induced cultures of the BE-deficient strain, KV832, harbouring pREP4-cm and plasmid indicated were analysed. The immunoblot analysis was done with antibodies prepared against wheat 87 kD SBEI. Migration of marker proteins revealed by amido black staining is shown to the right.

FIG. 7 shows an immunoblot analysis of starch granule-bound proteins.

A Analysis of starch granule-bound proteins by SDS-PAGE and silver staining. Migration of marker proteins (St) is shown to the left.

B Immunoblot analysis of starch granule-bound proteins using antibodies prepared against wheat 87 kD SBEI and SBEII. Migration of marker proteins revealed by amido black staining is shown to the right.

FIG. 8 shows SDS-PAGE analysis of starch granule proteins produced in wheat endosperm.

A Analysis of granule-bound proteins produced in developing endosperm of the hexaploid wheat cultivar, Fielder. Solid arrow indicates migration of SBEIc isoforms and open arrow shows migration of 59 kD GBSSII present in pericarp starch[21].

B SDS-PAGE analysis of granule-bound proteins extracted from mature kernels of *Triticum monococcum* Tm 23 (lane 1), *Triticum tauschii* accession PI 511-380 (lane 2), *Triticum turgidum* ssp. *durum* cultivar Kyle (lane 3) and *Triticum aestivum* cultivar Fielder (lane 4). Arrows indicates proteins recognised by SBEI antibodies and with similar migration as SBEIc.

Figure 9:
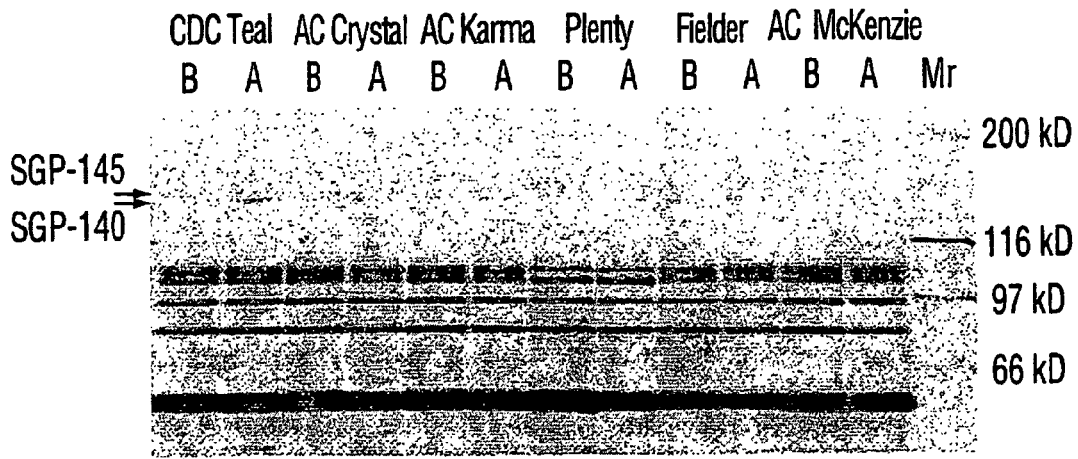

FIG. 9 shows SDS-PAGE analysis of SGP extracted from wheat A- and B-type starch granules. Each lane was loaded with protein extract from 5 mg A- and B-type starch granules of five hexaploid and one tetraploid (Plenty) cultivar. Separated proteins were visualised by silver staining and migration of protein molecular weight markers (Mr) is indicated to the right.

FIG. 10 shows analysis of starch granule size distribution in wheat endosperm.

A Light microscopic pictures (500×) of total starch granules harvested at different stages of endosperm development of the hexaploid wheat cultivar CDC Teal.

B Histogram of large-size (>10 µm) and small-size (<10 µm) granule size distribution during wheat endosperm development.

Figure 11A:
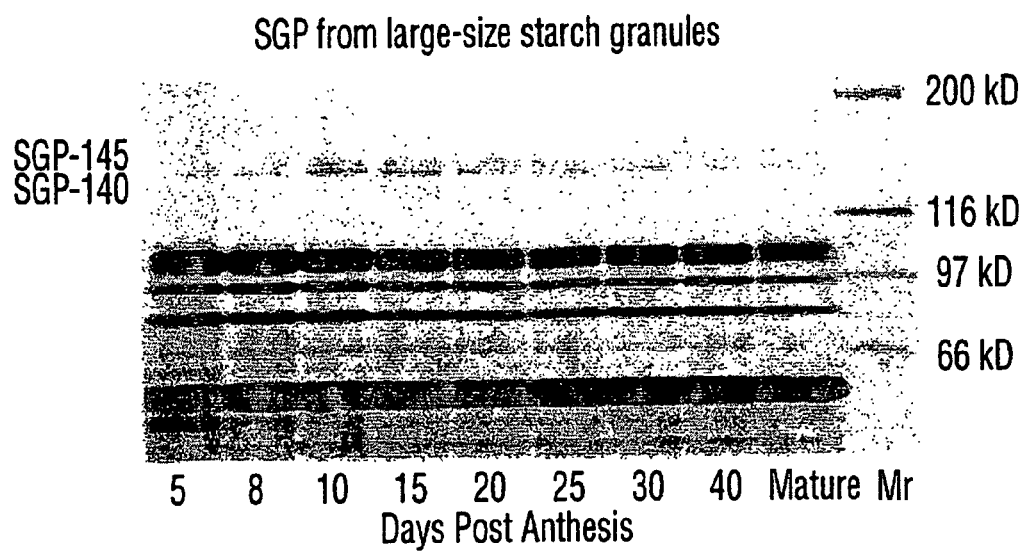
Figure 11B:
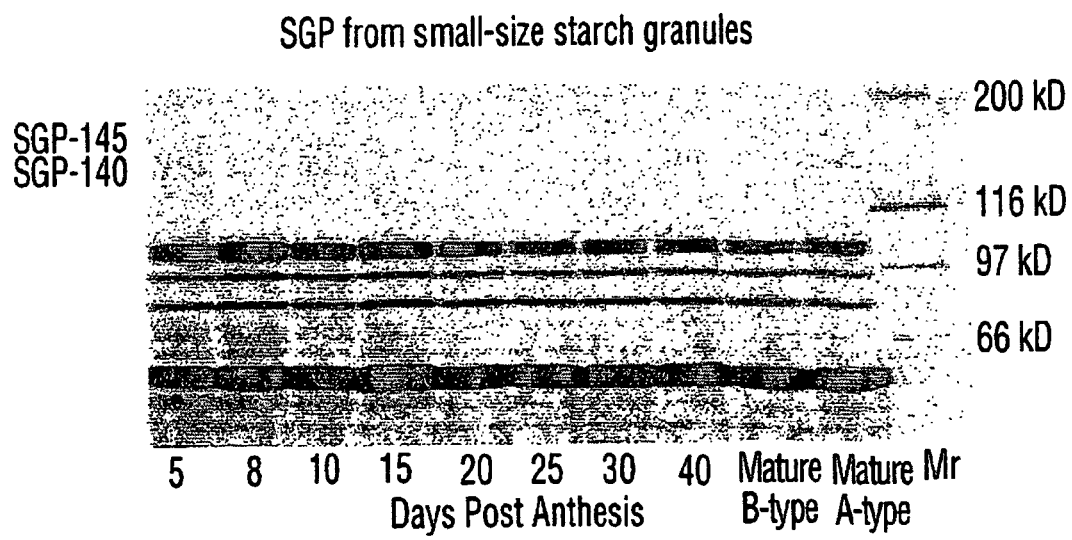

FIG. 11 shows SDS-PAGE analysis of SGP extracted from large-size (>10 µm) and small-size (<10 µm) starch granules of the hexaploid wheat cultivar CDC Teal. Samples of SGP from 5 mg starch granules were from different stages of wheat endosperm development as indicated. Gel-separated proteins were visualised by silver staining and migration of protein molecular weight marker (Mr) is indicated to the right.

Figure 12:
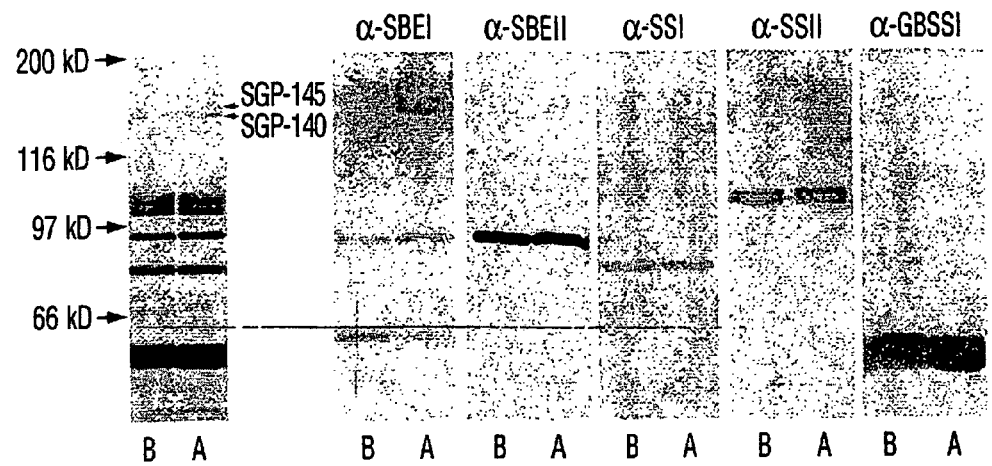

FIG. 12 shows immunoblot analysis of extracted SGP from wheat A- and B-type starch granules. Each lane was loaded with SGP extracted from 2 mg A- and B-type starch granules harvested from mature endosperm of the hexaploid wheat cultivar CDC Teal. To the left is shown SGP separated by SDS-PAGE and visualised by silver staining. To the right is shown immunoblot analyses of gel-separated SGP using polyclonal antisera prepared against different wheat starch biosynthetic enzymes as indicated.

Figure 13:
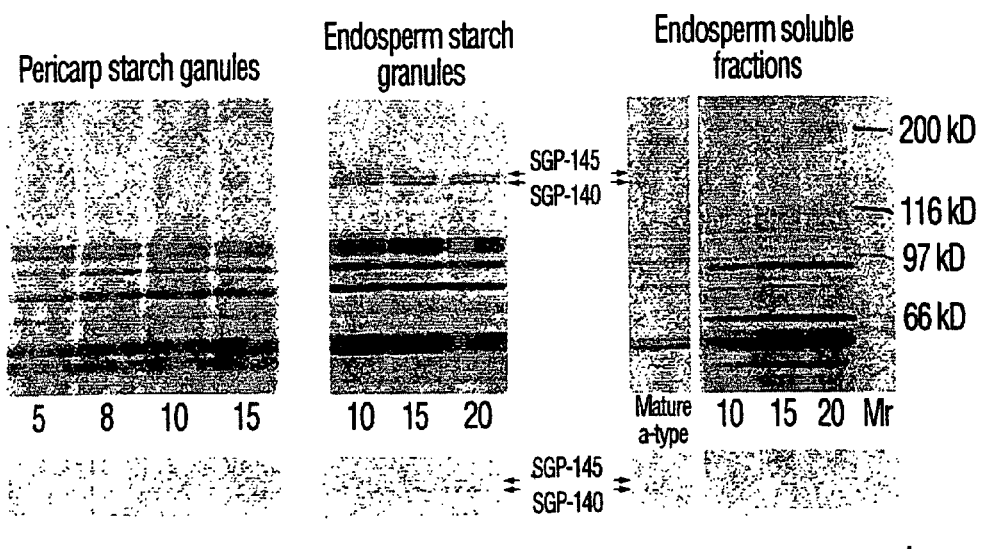

FIG. 13 shows sub-cellular localisation of SGP-140 and SGP-145 in immature wheat kernels.

SDS-PAGE analysis of SGP extracted from CDC Teal pericarp starch, endosperm starch and soluble endosperm proteins were prepared from different DPA of endosperm development as indicated. Samples of soluble protein [280 (10 DPA), 250 (15 DPA) or 250 (20 DPA) µg] and starch granules (5 mg) analysed were derived from the same amount of endosperm tissue. Gel-separated proteins were visualised by silver staining (pericarp and endosperm starch analysis) or Coomassie blue staining (soluble endosperm analysis). Migration of molecular weight marker (Mr) is shown to the right. Below is shown immunoreactive bands formed between gel-separated SGP-140 and SGP-145 and wheat SBEI antibodies.

FIG. 14 shows analysis of SGP in starches from various plant sources.

A SDS-PAGE analysis of SGP extracted from 5 mg starch of: A-type starch granules from endosperm of triticale, wheat, barley and rye; total starch from endosperm of canary seed, rice and maize; and potato tubers. Proteins were visualised by silver staining. Migration of molecular weight marker (Mr) is shown to the right.

B Immunoblot analysis of gel-separated proteins shown above. Immunoreactive bands obtained from interaction between wheat SBEI polyclonal antibodies and SGP-140 and SGP-145 are indicated.

C SDS-PAGE analysis of extracted SGP from 5 mg A- and B-type starches isolated from wheat, barley, rye and triticale endosperm. Proteins were visualised by silver staining. Migration of molecular weight marker (Mr) is shown to the right.

The inventors have characterised a cDNA encoding a novel form of SBEI in wheat endosperm. The encoded polypeptide was found to be preferentially associated with A-type starch granules.

Isolation of a Partial SBEI cDNA Clone

Figure 1:
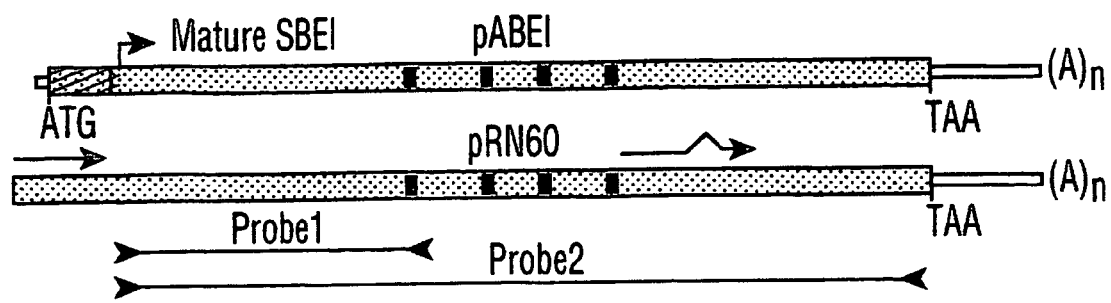
FIG. 1 shows a schematic alignment of pABEI and pRN60 cDNA. Hatched area of pABEI coding region (grey box) represents sequence encoding a putative transit peptide and horizontal arrows on the pRN60 cDNA show location of imperfect direct repeats. The four black areas within the coding region represent sequences encoding the highly conserved regions of enzymes belonging to the α-amylase family[11]. DNA fragments used as probes in DNA and RNA hybridisations are indicated below.

During screening of a wheat (*Triticum aestivum* L. cv. Fielder) cDNA library for Sbe1 clones using probe 1, the pRN60 clone was isolated (FIG. 1). DNA sequence analysis of pRN60 revealed a 2962 bp insert that was 162 bp longer than a previously characterised full-length SBEI cDNA, pABEI, isolated from the same library (FIG. 1)[19]. The two cDNA clones matched almost perfectly from the 3' end to 346 nucleotides from the 5' end of the pRN60 cDNA (99.8% nucleotide identity and 100% encoded amino acid identity), at which point the two sequences diverged. In contrast to the pABEI cDNA, the 346 bp 5' sequence of pRN60 cDNA did not seem to encode a transit peptide, but instead matched sequences located further downstream on the same cDNA. The unusual 5' sequence carried by pRN60 lacked stop codons in frame with the downstream SBEI coding region, which suggested that the isolated cDNA could be translated from the first base, and therefore, might not represent a full-length transcript.

RNA Blot Analysis of Wheat Endosperm Reveals Two Sbe1 Transcripts

The existence of Sbe1 transcripts that were longer than those encoding the 87 to 88 kD SBEI isoforms was confirmed by an RNA gel blot analysis. This analysis of wheat kernel RNA extracted at various time points during kernel development showed that a transcript of about 5 kb, in addition to the expected 2.8 Sbe1 mRNA, was recognised by the Sbe1-specific probe (FIG. 2A). The signals from both the 5 and 2.8 kb transcripts were very weak in samples of five-day-old kernels, in which the endosperm is very immature, but were clearly seen in samples prepared from 10- to 25-day-old kernels. In kernels younger than 10 days post anthesis (DPA), the 5 kb hybridisation signals appeared stronger as compared to the signal from the 2.8 kb transcript.

Isolation of Full-length cDNA Corresponding to 4.6 kb Sbe1 Transcript

With the hypothesis that the pRN60 cDNA was a partial product of the about 5 kb Sbe1 transcript, the inventors isolated the 5' end of this mRNA species using a 5'-RACE procedure. Gel analysis of products obtained from the final PCR reaction revealed one major fragment of 1.9 kb and three minor fragments (FIG. 3B, lane AP2+BE39). No products were obtained from control reactions employing only one primer (FIG. 3B; lanes AP2 and BE39). The different PCR products were analysed by DNA sequencing, which showed that only the 1.9 kb fragment carried Sbe1-like sequences. One of the 1.9 kb 5'-RACE products was found to correspond 100% to the 272 bp region overlapping the 5' end of pRN60, and the composite cDNA sequence obtained with this product and the pRN60 cDNA gave a 4563 bp long sequence. This assembled sequence was denoted Sbe1c to distinguish it from the inventors' previously characterised wheat Sbe1 clones, Sbe1a[17] and Sbe1b[19].

The 5'-RACE analysis suggested that several variants of the 4.6 kb Sbe1c transcript were produced in the wheat endosperm. RT-PCR analysis using the BE65/BE38 primer pair (FIG. 3A) and endosperm RNA further confirmed this observation. The 2.0 kb RT-PCR products generated from three independent RT-PCR experiments (FIG. 3C, lane BE65+BE38) were found to be of at least three different variants, that differed slightly in deduced amino acid sequence. One of the sequence variants matched exactly to the corresponding sequence on Sbe1c, and thus, independently confirmed the 2.0 kb 5' sequence of Sbe1c.

The 4563 bp SBEI cDNA Encodes a Protein With Two SBEI-like Domains

DNA sequence analysis of the 4563 bp Sbe1c cDNA (FIG. 4, and SEQ. ID NO: 1) revealed an open reading frame of 1425 codons that was initiated from the 5' end of the assembled sequence and terminated at nucleotides 4278–4280. The TAA stop codon was followed by a possible polyadenylation signal sequence, AATAAA, located 19 bp upstream of the polyadenylation tail. Initiation of translation was assigned for the first ATG codon (nucleotides 63–65), allowing translation of 1405 codons of the open reading frame. Sequence analysis of the proposed amino-terminal region of SBEIc revealed a 50% sequence identity to transit peptides predicted from wheat Sbe1a and Sbe1b. Thus, SBEIc appeared, like the 87 kD SBEI, to be imported into plastids. Cleavage of the transit peptide was proposed to occur between amino acids $Ala_{67}$ and $Ala_{68}$ of the deduced SBEIc sequence (Ile-Ala-Ala↓Ala), as this site showed high resemblance to the consensus sequence for transit peptide cleavage sites, Val/Ile-X-Ala/Cys↓Ala[22]. Processing of the SBEIc precursor would leave a 1338 amino acid long mature protein with a calculated molecular mass of 152 kD. The transit peptide cleavage site was confirmed by N-terminal sequencing of SBEIc isoforms produced in the wheat cultivar Teal (data presented further below in Table 1).

endosperm[18]. The proposed translational start codons coincided for wSBEI-D2 and SBEIc cDNA, but no sequence corresponding to the 57 long carboxy-terminal residues of wSBEI-D2 was present on SBEIc.

The first domain of SBEIc and the corresponding sequence on wSBEI-D2 differed from other characterised SBEI from plants at the four highly conserved regions on enzymes belonging to the α-amylase family, which include plant SBE[11]. It was especially notable that the Asp residues on regions two and four and the Glu residue on region three, all proposed to be directly involved in hydrolysis of α-1,4 glucan bonds[11], were replaced by non-equivalent residues (FIG. 5).

Expression of Sbe1c Complements a BE Mutation in *Escherichia coli*

To examine if the isolated cDNA encoded an active enzyme, a prokaryotic expression vector, pQE-SBEIc, encoding a histidine-tagged mature SBEIc (amino acids 1–1338) was constructed (FIG. 6A) and tested for activity in a *Escherichia coli* BE-deficient mutant, KV832[23]. Since high level expression of the His-tagged SBEIc was found to severely affect cell growth, a construct expressing the Lac repressor (pREP4-cm) was also introduced into the cells to control transcription from the strong T5 promoter. SDS-PAGE and immunoblot analysis of extracts prepared from the transformed KV832 cells confirmed that a polypeptide of expected molecular mass (154 kD) was produced at a very low level in non-induced cells, but was clearly seen in cells induced with IPTG for two hours (FIG. 6C, lane 4). The BE-mutant carrying pREP4-cm and cloning vector pQE30 showed a blue/grey colour upon iodine staining, indicating low or no branching of the glucan polymers (FIG. 6B).

TABLE I

Alignment of SGP-140 and SGP-145 N-terminal sequences to those predicted for wheat endosperm SBEI and SBEI-like proteins

| Polypeptide | Sequence |
|---|---|
| SGP-140 | K/H  I/V          R  R    R  M    R |
| SGP-145 | Q              M |
| SBEIc (152 kD) | A              M |
| wSBEI-D2 (87 kD) |            I |
| SBEIb (87 kD) | V S A P R D Y    A E D  V G D    I |

Wheat wSBEI-D2 is an SBE-like protein predicted to be produced in wheat endosperm[18] and SBEIb is deduced N-terminal sequence of 87 kD SBEI expressed in wheat endosperm[19]. Identical amino acids are highlighted.

Analysis of the deduced mature SBEIc sequence disclosed the presence of two SBEI-like sequences, domain 1 and 2, encompassing amino acids 1–561 and 570–1338, respectively, on the mature SBEIc (FIG. 5). As already mentioned, the sequence of the second domain was identical to that of the mature protein encoded by the pABEI cDNA. The main difference between the first domain and the second domain was the lack of a 21 and a 163 amino acid long sequence on domain 1. These two sequences corresponded to exon nine and exons 11 to 14, respectively, on wheat genomic DNA coding for the 87 kD SBEI (FIG. 5). Further analysis of SBEIc showed that the first domain including the transit peptide was very similar to the first 629 amino acids (92% identical residues) of a 686 amino acid long SBEI-like protein, wSBEI-D2, presumed to be produced in the wheat Expression of pQE-SBEIc in KV832 cells harbouring pREP4-cm resulted in a brown colour upon iodine staining, showing that the BE-mutant had regained the ability to branch glucan molecules. The BE-positive strain, DH5α, transformed with pREP4-cm and pQE30A gave a yellow/brown colour upon treatment with iodine, as expected from a strain able to produce glycogen-like polymers. The slight differences in iodine staining patterns of cells producing plant and bacterial BE has been suggested to reflect differences in enzyme specificity[24]. Production of BE activity from cells expressing Sbe1c was confirmed by the phosphorylase α assay[20], which revealed a >90-fold higher level of BE activity in soluble cell extracts of non-induced KV832 cells harbouring pQE-SBEIc, as compared to KV832 cells lacking this construct (FIG. 6B). The BE-positive strain, DH5α, produced a 4.5 times lower level of BE activity than the complemented KV832 cells. The BE activity in induced cells expressing Sbe1c was not assessed, since most of the produced SBEIc in these cells was deposited into inclusion bodies.

The 152 kD SBEI is Associated with Starch Granules of the Wheat Endosperm

To test if the granule-bound protein of about 149 kD reported by Schofield and Greenwell (1987)[25] could correspond to SBEIc, the inventors analysed starch granule extracts by SDS-PAGE and immunoblotting. Silver-staining of extracted and gel-separated proteins from granules of mature hexaploid wheat kernels resolved seven clearly visible protein bands, of which one band migrated as a 140 kD protein in the gel system used (FIG. 7A). An immunoblot analysis of the gel-separated proteins using polyclonal antiserum prepared against the wheat 87 kD SBEIb confirmed that the 140 kD protein band was related to SBEI (FIG. 7B, lane α-SBEI). The immunoblot analysis also revealed an interaction with the 92 kD protein band and several 62 to 67 kD protein bands of unknown identities. Since the 140 kD granule-bound protein corresponded reasonably well in mass to SBEIc and no SBEI corresponding in mass with SBEIc was found by immunoblot analysis of the soluble endosperm (data presented in FIG. 13), the inventors reasoned that SBEIc was incorporated into starch granules. Further analysis of the granule-bound proteins using polyclonal antibodies prepared against a 87 kD wheat SBEII, revealed only an interaction with the 92 kD protein band (FIG. 7B, lane α-SBEII), as previously reported by Rahman et al. (1995)[26]. Thus, isoforms analogous to SBEIc and bound to starch granules did not seem to exist for SBEII in wheat.

Figure 2:
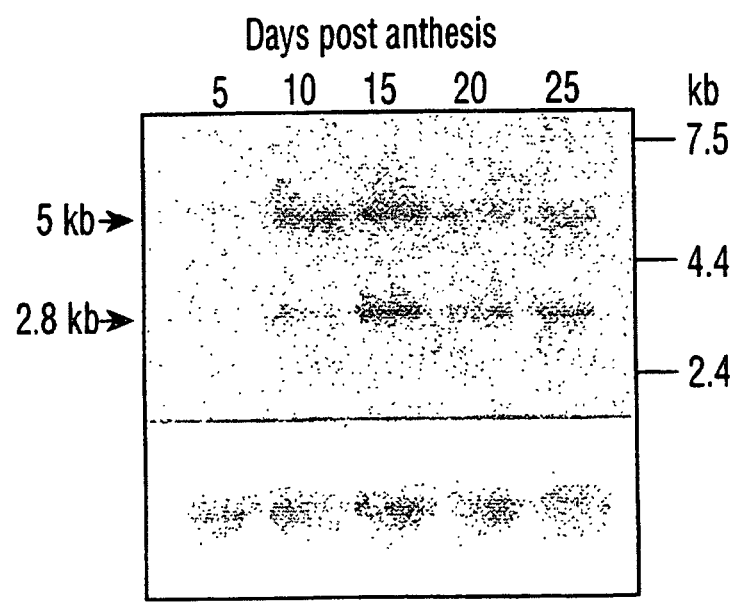
FIG. 2 shows RNA gel analysis of Sbe1 expression during wheat kernel development.
Figure 8A:
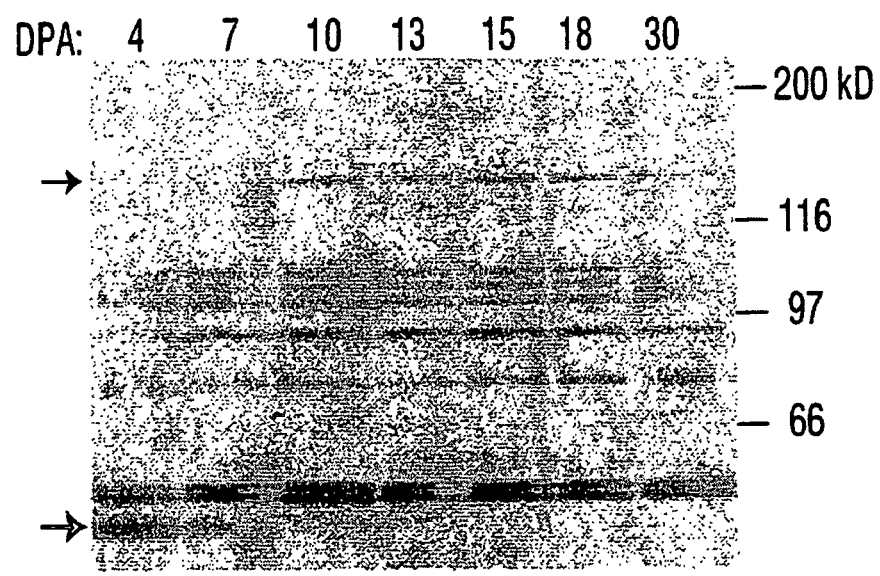

A gel analysis of granule-bound proteins extracted from developing kernels at different stage after anthesis showed no presence of the 140 kD protein band in starch prepared from kernels that were less than five days old. These young kernel samples contained a substantial amount of pericarp starch, as indicated by the presence of the 59 kD GBSSII[21] (FIG. 8A). The 140 kD protein band appeared in total kernel starch between five and seven DPA and its abundance was relatively constant from there on. Thus, the accumulation of the large isoform of SBEI in the kernel starch coincided with the accumulation of the 4.6 kb SBEI transcript during kernel maturation (FIG. 2).

One or two proteins corresponding closely in migration with SBEIc were also found associated with starch granules of *Triticum monococcum, Triticum tauschii* and *Triticum turgidum* ssp. *Durum* (FIG. 8B), and immunoblot analysis confirmed that these proteins were recognised by SBEI antibodies. The inventors concluded that SBEIc isoforms must be encoded by all three genomes of hexaploid wheat.

The inventors have further demonstrated that SBEIc and its isoforms are preferentially associated with A-type starch granules of wheat endosperm.

SBEIc Isoforms are Preferentially Associated with A-type Starch Granules in Wheat Endosperm The inventors compared starch granule proteins (SGPs) localised in A- and B-type starch granules, by purifying the two granule fractions from wheat endosperm of six wheat cultivars using a method previously reported[27]. The extracted SGPs were resolved by SDS-PAGE and visualised by silver staining. To quantitatively compare the different polypeptides in A- and B-type starch granules, the 60 kD GBSSI was used as an internal standard for equal loading of proteins. The major SGP of 60, 80, 92, 100, 108 and 115 kD, were present in similar concentrations in A- and B-type starch granules from all the cultivars tested (FIG. 9), and no difference was observed among polypeptides with molecular masses lower than 60 kD. These results were consistent with previous studies that reported almost identical polypeptide profiles for wheat A- and B-type starch granules[48,26,29].

In addition to known SGPs, the inventors found that A-type starch granules of all wheat cultivars tested contained a polypeptide co-migrating with SBEIc of Fielder (FIG. 9). A slightly larger polypeptide, with an apparent molecular mass of 145 kD, was also present in A-type starch granules of all cultivars except Fielder (FIG. 9). Analysis of B-type starch granules from the six wheat cultivars showed a much lower abundance of the 140 and 145 kD polypeptides as compared to the A-type granules. In B-type granules of the cultivar Fielder, only the 140 kD band was observed. Thus, the inventors concluded that SGP-140 band, which includes SBEIc in Fielder, and SGP-145 are preferentially associated with A-type starch granules.

Figure 10A:
Figure 10B:
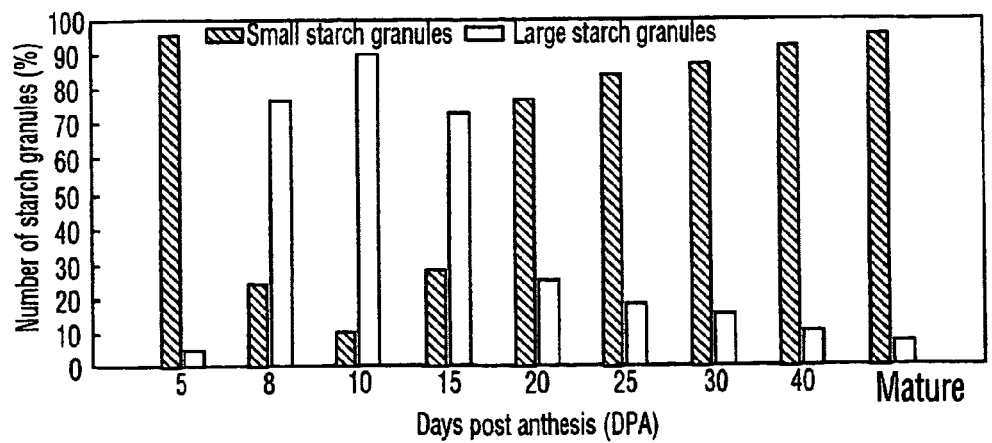

In developing wheat endosperm, A-type starch granules are initiated at about four to 14 DPA, whereas B-type granules are formed after 14 DPA[4,30]. After initiation, both granule types continue to grow until maturity of the endosperm[31]. An image analysis of purified large-size and small-size starch granule fractions from developing endosperm of the cultivar CDC Teal showed that the growth of small starch granules formed before and after 15 DPA was significantly different (FIG. 10). Prior to 15 DPA, the newly formed small starch granules grew rapidly in size to become large-size (>10 µm) starch granules (FIG. 10A). During the time period eight to 15 DPA, large-size starch granules accounted for more than 70% of total endosperm starch granules (FIG. 10B). Small-size starch granules formed after 15 DPA increased rapidly in number until maturity (from 25% to 94%), but they grew very slowly and only reached diameters less than 10 µm.

SGP-140 and SGP-145 are Preferentially Incorporated into A-type Starch Granules Throughout Endosperm Development The preferential incorporation of SGP-140 and SGP-145 into A-type granules can be explained by synthesis of these polypeptides only during the first 15 DPA. To study this possibility, the inventors analysed the protein profiles of large-size and small-size granules isolated at different DPA (FIG. 11). The large-size (>10 µm) A-type starch granules were found to show no variation in SGP-140 and SGP-145 concentration during development. Small-size starch granules (<10 µm in diameter) formed before 15 DPA, which were of the A-type, were also found to contain SGP-140 and SGP-145 at about the same concentration as in large-size granules. On the other hand, small-size B-type starch granules harvested after 15 DPA, showed very low presence of SGP-140 and SGP-145. The analyses demonstrated no significant variation in concentration of the other major granule-bound polypeptides (60, 80, 92, 100, 108 and 115 kD) for both small-size and large-size starch granules throughout endosperm development. In the cultivar CDC Teal, most of the A-type granule growth occurred after 15 DPA, when about 65% (w/w) of the starch in A-type granules was synthesized. The constant levels of SGP-140 and SGP-145 in A-type granules strongly suggested that the two proteins were continuously incorporated into A-type granules throughout endosperm development.

The ratio of total SGP-140 plus SGP-145 in A-type granules versus total SGP-140 plus SGP-145 in B-type granules is preferably at least about 4, more preferable at least about 5, most preferably at least about 10.

Both SGP-140 and SGP-145 are Related to SBEI

To confirm the identity SGP-140 as an SBEI isoform in the cultivar CDC Teal and to identify SGP-145, immunoblots of SGP from A- and B-type starch granules were reacted with polyclonal antibodies raised against wheat SBEI, SBEII, SSI, SSII and GBSSI, respectively (FIG. 12). The major polypeptides of 60 kD (GBSSI), 80 kD (SSI), 92 kD (SBEII) and 100 to 115 kD (SSII), were recognised by their respective antibodies, as expected, with no difference in intensity between A-type and B-type granules. Among the five antibodies tested, only the wheat SBEI antibodies reacted with SGP-140 and were also found to recognise SGP-145. A weaker interaction between the SBEI antibodies and a protein co-migrating with SBEII and proteins of approximately 63 kD were also seen. Similar to the analysis of SGP-140 and SGP-145 by SDS-PAGE, the immunoreactive bands were strong in A-type, but weak in B-type starch granules.

The inventors have further confirmed that SGP-140 and SGP-145 protein bands of the wheat cultivar CDC Teal have very similar N-terminal sequences as SBEIc. Direct amino acid sequencing of the protein bands purified from SDS-PAGE gels suggested variation in amino acid sequence as indicated in Table I. This is likely due to presence of several polypeptides that differ slightly in sequence within the same protein band. Presence of several isoforms of SBEIc was also suggested by reverse transcription PCR analysis of transcripts produced in the cultivar Fielder. Alignment of the determined N-terminal sequences of the SGP-140 and SGP-145 with those predicted for SBEIc and wSBEI-D2 revealed striking similarities, thus suggesting that all four polypeptides were closely related (Table I). A lower level of similarity was noted to the predicted N-terminal sequence for the wheat 87 kD SBEIb[19] isoform. Since the molecular masses of SGP-140 and SGP-145 were reasonably close to that of SBEIc (152 kD) predicted from Sbe1c cDNA, the inventors concluded that SGP-140 and SGP-145 bands contain isoforms of SBEIc.

SGP-140 and SGP-145 are Only Located to Starch Granules in the Wheat Endosperm

To localise SGP-140 and SGP-145 in the developing kernels, SGP from pericarp and endosperm starch granules, and the soluble endosperm fraction were prepared from developing wheat kernels, and analysed by SDS-PAGE and immunoblotting (FIG. 13). The results of these analyses confirmed that SGP-140 and SGP-145 were present within the endosperm starch granules, but could not be found in the endosperm soluble fraction. Nor were SGP-140 and SGP-145 observed in pericarp starch granules harvested from 5 to 10 DPA, but could be seen as two very faint bands in pericarp granules of 15 DPA. Since pericarp from kernels older than 15 DPA was rather difficult to separate from the endosperm, it is possible that the two faint bands seen in 15 DPA pericarp sample originated from some endosperm starch granules mixed with the pericarp starch granules.

Figure 14A:
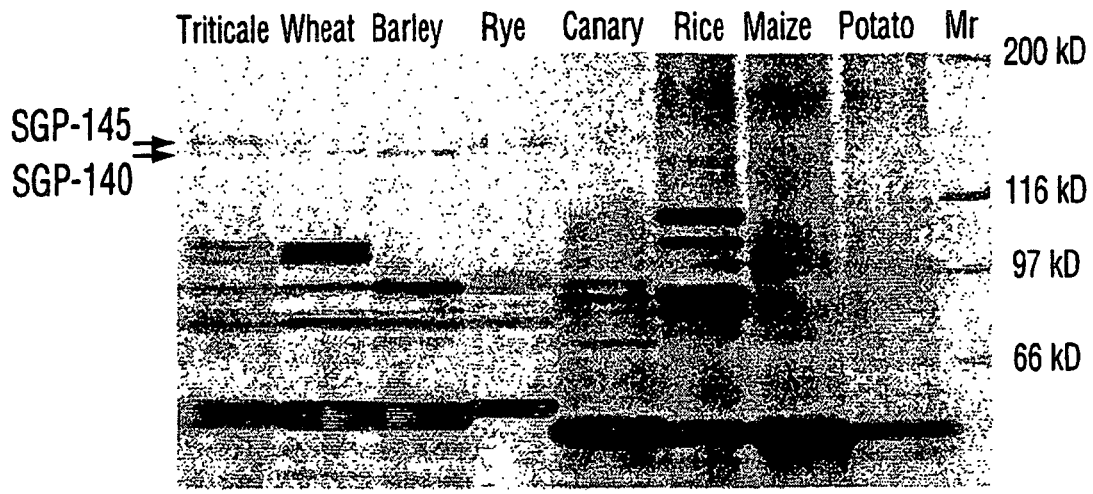
Figure 14B:
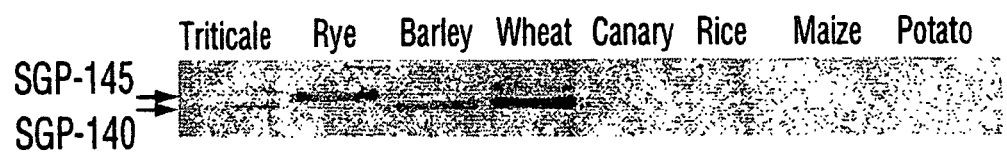

SGP-140 and/or SGP-145 Homologues Exist in Plant Species Known to Produce A- and B-type Starch Granules The inventors' study included starches from plants with bimodal (rye, barley and triticale) and unimodal (rice, maize, potato, canary seed) starch granule size distribution[1]. SDS-PAGE analysis of extracted SGP from triticale, barley and rye revealed one (barley and rye) or two protein bands (triticale) with similar relative mobility as SGP-140 and SGP-145 of wheat (FIG. 14A). These protein bands were also found to react with SBEI antibodies (FIG. 14B), and thus appeared to be SGP-140 and SGP-145 homologues. Analysis of canary seed, rice, maize and potato SGP did not reveal presence of any polypeptides similar in size to SGP-140 and SGP-145 and reacting with SBEI antibodies (FIGS. 14A and 14B). Thus, it appeared that proteins similar to SGP-140 and SGP-145 were only present in cereal starches with bimodal granule size distribution.

Figure 14C:
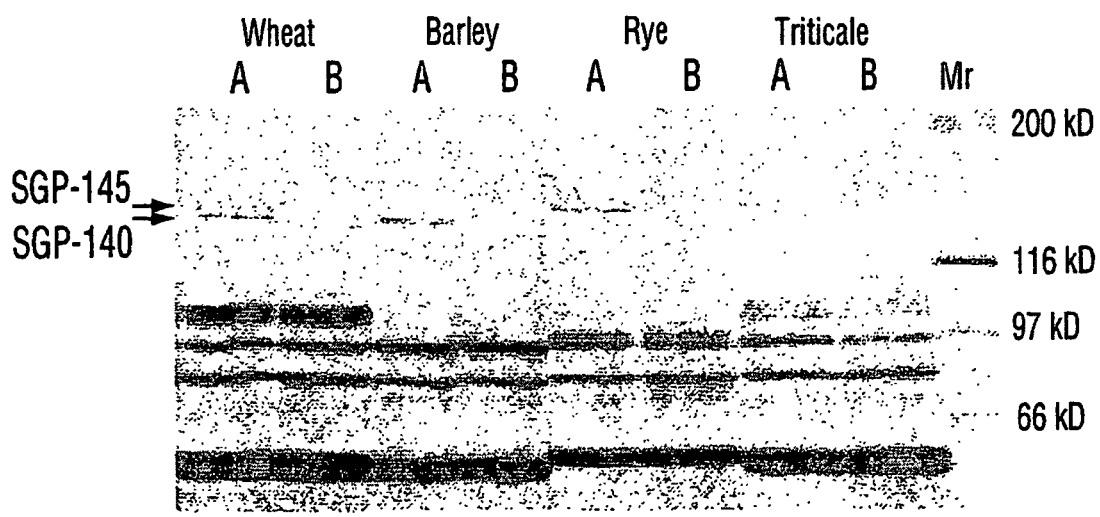

To determine if the SGP-140 and SGP-145 counterparts in triticale, barley and rye were, like in wheat, preferentially associated with A-type starch granules, the A- and B-type starch granules from these cereals were analysed. Similar to wheat endosperm starch, the SGP-140 and SGP-145 homologues were abundant in A-type starch granules, but very scarce in B-type starch granules (FIG. 14C).

The results show that SGP-140 and SGP-145 are preferentially found on both small-size and large-size A-type granules (FIG. 11). No reduction was noted in SGP-140 and SGP-145 concentrations in large granules harvested after 15 DPA (FIG. 11), a developmental stage when most of the A-type granule starch is being produced. This suggests that SGP-140 and SGP-145 are continuously targeted to A-type granules, even when B-type granules are produced. Since SGP-140 and SGP-145 did not accumulate in the soluble phase of the endosperm, these proteins must be actively produced both before and after 15 DPA. This was also indicated by RNA analysis of SGP-140 gene expression during kernel development, which showed only a small reduction in transcript levels after 15 DPA, as compared to before 15 DPA (FIG. 2).

The inventors demonstrated that the 140 kD protein band revealed by SDS-PAGE analysis of Fielder wheat starch granules contains a novel 152 kD isoform of SBEI in plants. SBEIc encoded by the isolated cDNA differed from previously characterised SBEI isoforms by its high molecular mass and by the presence of two domains of SBEI-like sequences. Domain 1 differs from domain 2 by the lack of a 21 amino acid long peptide and a 163 residue long (~17 kD) C-terminal sequence (FIG. 5).

The inventors study showed that the 152 kD SBEIc represents a granule-bound form of SBEI.

Figure 8B:
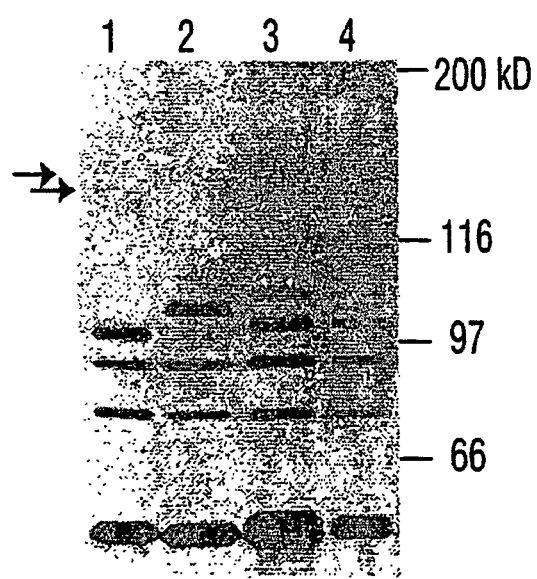

The analysis of SBEI transcripts produced in the developing wheat endosperm of the cultivar Fielder suggested that there are at least three different forms of SBEIc transcripts produced. These variants would encode proteins of very similar molecular masses (<1 kD difference), and thus, cannot be distinguished as separate bands on one-dimensional SDS-PAGE gels. Our analysis of starch granules of *Triticum* species suggested that variants of SBEIc also exist in both diploid (*Triticum monococcum, Triticum tauschii*) and tetraploid (*Triticum turgidum* ssp. *durum*) wheat (FIG. 8B). For the tetraploid wheat cultivar Kyle, two separate protein bands were distinguished, and apparently, the difference between the SBEIc isoforms in this cultivar is more distinguishable on SDS-PAGE gels than those of the hexaploid wheat cultivar Fielder.

INDUSTRIAL APPLICABILITY

SEBIc is a novel starch branching enzyme. It can be used in vitro to synthesise or modify starch. Modified starches find use in the food and beverage industries as a thickener and sweetener, as well as in industrial uses, such as the production of stiffening agents for laundering, sizing for paper and as thickening agents and adhesives[32,33].

The Sbe1c sequence, or fragments thereof, or complementary sequences to any of these can be used to screen plant genomes to locate genes that are homologous (i.e. which encode similar activities).

Expression of SBEIc in a plant can be expected to result in modification of starch granule morphology and size distribution in seed endosperm. The Sbe1c gene may be expressed in a plant already having a copy of this gene, in which case the expression SBEIc can be expected to increase. Increase in SBEIc expression may result in increase in A-type starch granule concentration, and/or in increase in starch granule size. Cultivars having increased A-type granules would be desirable, for example, in the production of gluten, as A-type granules are more easily separated from the protein of the endosperm. Wheat starch with elevated A-granule content has applications in the manufacture of biodegradable plastic film and carbonless copy paper[34].

In addition to the sequence of Sbe1c, listed in SEQ ID NO: 1, the invention also relates to homologous variants of SEQ ID NO: 1, including DNA sequences from plants encoding proteins with two SBEI-like domains, as illustrated in FIG. 5, and deduced amino acid sequences of 25% or greater identity, and 40% or greater similarity, isolated and/or characterised and/or designed by known methods using the sequence information of SEQ ID NO:1 or SEQ ID NO: 2, and to parts of reduced length that are able to function as inhibitors of gene expression by use in an anti-sense, co-suppression [Transwitch® gene suppression technology; U.S. Pat. No. 5,231,020, Jul. 27, 1993; for reviews see Iyer et al. (2000)[35], Baulcombe (1996)[36] and Vaucheret et al. (1998)[37]] or other gene silencing technologies. It will be appreciated by persons skilled in the art that small changes in the identities of nucleotides in a specific gene sequence may result in reduced or enhanced effectiveness of the genes and that, in some applications (e.g. anti-sense or co-suppression), partial sequences often work as effectively as full length versions. The ways in which the gene sequence can be varied or shortened are well known to persons skilled in the art, as are ways of testing the effectiveness of the altered genes. All such variations of the genes are therefore claimed as part of the present invention.

Other preferred degrees of identity to the indicated sequences are at least 30%, 40%, 50%, 60%, 70%, 80%, 90% and 95%; and other preferred degrees of similarity are at least 50%, 60%, 70%, 80%, 90% and 95%. To assess sequence homology, a computer program known as MegAlign®, DNASTAR® of DNASTAR Inc., 1228 South Park Street, Madison, Wis. 53715, USA, may be used. This program is based on the Clustal V algorithm[38]. For each gap introduced in the alignment, the program deducts a penalty from the score. A higher gap penalty suppresses gapping; a lower value promotes it. The program also assesses penalties based on the length of the gap. The more residues the gap spans, the greater the penalty. The program deducts these penalties from the overall score of the alignment.

The expression "homologous variant", when referring to a DNA sequence, encompasses all DNA sequences encoding a protein having the same functionality as the recited sequence, as well as those having two SBEI-like domains, illustrated in FIG. 5. The same expression, when referring to an amino acid sequence, encompasses all amino acid sequences having the same functionality as the given sequence.

Suppression of transcription and/or translation of Sbe1c, for example, by using anti-sense approaches, would be expected to reduce the concentration of A-type starch granules. Reduction in A-type granules is desirable if the starch is going to be used as face powder, as a laundry-stiffening agent, a fat replacement or in the production of degradable plastic films[39, 40].

For the purposes of breeding cultivars having enhanced A-type starch granule concentration, probes based on the sequence of Sbe1c (SEQ ID NO: 1) or complementary sequences may be used to screen the genome of existing cultivars to find those cultivars having within their genome homologues (particularly alleles) of Sbe1c, encoding SBEs that are preferentially bound to A-type starch granules. Such cultivars can be chosen for crossbreeding with one-another, resulting in progeny strains having a high level of SBEIc or homologue expression. Alternatively, cultivars having a low level of Sbe1c-like sequences within their genome can be expected to have a low level of A-type starch granules. Such cultivars could be chosen for crossbreeding with one-another, resulting in progeny strains having a low level of SBEIc expression, and a reduced content of A-type starch granules.

Similarly, strains expressing SBEIc or homologous variants can be found using antibodies raised to SBEIc (polyclonal or monoclonal) to screen cereal varieties to find those having SBEIc or variants. Antibodies to SBEIc can be produced by known methods[41, 42, 43, 44].

The invention also relates to a method of genetically transforming a plant so that the plant expresses a starch branching enzyme that is bound to A-type starch granules in wheat, barley, or triticale endosperm.

The invention further relates to a genetically modified plant expressing a starch branching enzyme that is bound to A-type starch granules in wheat, barley, or triticale endosperm.

The invention also relates to a genetically modified plant having within its genome a hybrid gene, wherein the hybrid gene comprises a DNA sequence encoding a starch branching enzyme that is bound to A-type starch granules in wheat, barley or triticale endosperm, or a fragment thereof, fused to a passenger-gene. The protein encoded by the hybrid gene is preferably targeted to starch granules. The passenger-gene preferably encodes a vaccine, an antibody, a pigment, a preservative, a fragrant or flavour inducing agent, a receptor, or an enzyme involved in lipid, carbohydrate or protein synthesis, degradation or modification.

Genetically modified plants expressing SBEIc activity would be expected to have altered starch granule morphology. In plants having unimodal starch granule deposition in the wild type, the transformant could be expected to be either bimodal (i.e. large and small starch granules), or unimodal, but with an increase in starch granule size.

Methods for transforming plants are known in the art [see, for example, Potrykus (1991)[45]; Vasil (1994)[46]; Walden and Wingender (1995)[47]; Songstad et al. (1995)[48]; Bechtold et al. (1993)[49]; Katavic et al. (1994)[50]; DeBlock et al. (1989)[51]; Moloney et al. (1989)[52]; Sanford et al. (1987)[53]; Nehra et al. (1994)[54]; Becker et al. (1994)[55]; Rhodes et al. (1988)[56]; Shimamoto et al. (1989)[57]; Meyer, (1995)[58]; Datla et al. (1997)[59]].

BEST MODES FOR CARRYING OUT THE INVENTION

Abbreviations

DTT: diothiothreitol
EDTA: ethylene diammine tetraacetate
IPTG: isopropyl β-D-thiogalactopyranoside 5'-RACE: 5'-rapid amplification of cDNA ends
RT-PCR: reverse transcription-polymerase chain reaction
SDS: sodium dodecyl sulfate
Tris: tris(hydroxymethyl)aminomethane Screening of a Wheat cDNA Library Approximately 200,000 plaques of a cDNA library, constructed from wheat poly(A)+ RNA isolated from 12-day-old wheat kernels[60], were screened for Sbe1 clones by plaque hybridisation[61]. Probe 1 used in the library screening consisted of an 828 bp Reverse Transcription-PCR (RT-PCR) product, obtained from a reaction using 12 day old wheat kernel RNA and the Sbe1-specific primers BE11 and BE12 (FIGS. 1 and 4). The primers were based on sequences of previously characterised Sbe1 clones from wheat[17][19]. Ten of the positive clones were plaque-purified and their inserts were excised in vivo from the Uni-ZAP XR™ vector (Stratagene). The clone with the longest insert was denoted pRN60 and chosen for further characterisation.

DNA Sequence Analysis

Templates for sequencing were prepared by subcloning DNA fragments into the pBluescript II SK+ vector (Stratagene). DNA sequencing reactions were performed by the dye terminator cycle sequencing technique and analysed on an automated DNA Sequencer (Applied Biosystems, Foster City, Calif.). All reported sequences were determined on both strands and from overlapping templates. Nucleotide sequences were assembled and analysed using the Lasergene™ software (DNASTAR. Inc.). Pair-wise alignments of DNA and protein sequences were calculated by the Clustal method using a ktuple value 1, gap penalty value 3 and window size 5.

Isolation of RNA and RNA Gel Blot Analysis

Total RNA was isolated from 12-day-old wheat kernels using a hot-phenol method as described[62]. RNA gel blot analysis was performed with 20 µg total RNA fractionated on a 1% agarose-2.2 M formaldehyde gel, transferred to a Hybond™ (Amersham) membrane, hybridised with probe 2 (nucleotides 1993 to 4209 of Sbe1c; FIG. 1) and washed as described by Nair et al. (1997)[60]. To assure that about the same amount of RNA was loaded onto each lane, the hybridised blot was stripped and rehybridised with a 25S ribosomal DNA probe as described[60]. Probes were radiolabelled using the Rediprime™ random primer labelling kit from Amersham.

5'-RACE

5'-RACE was performed with poly(A)+ RNA extracted from 12-day-old wheat endosperm following the protocol supplied with the Marathon™ cDNA Amplification Kit from Clontech. The first strand synthesis was primed with the Sbe1-specific BE19 primer (FIGS. 3 and 4) After synthesis of the second strand, the double-stranded cDNA was ligated to the Marathon cDNA Adapter (Clontech), followed by a first round PCR amplification performed with the adapter primer AP1 (5'-CCATCCTAATACGACTCACTAT-AGGGC-3'; Clontech) and the Sbe1-specific primer BE25 (FIGS. 3 and 4). The reaction was initiated by a denaturation step at 94° C. for 3 min followed, by 25 cycles of 94° C. 30 sec, 62° C. 20 sec and 68° C. 3 min and a final 10 min extension at 68° C. Products derived from the 4.8 kb Sbe1 transcripts were separated from shorter products derived from the 2.8 kb Sbe1 mRNA by agarose gel electrophoresis. Products of 1.9 to 2.7 kb were gel-purified and used as a template in a nested amplification employing nested adapter primer AP2 (5'-ACTCACTATAGGGCTCGAGCGGC-3'; Clontech) and the gene-specific primer BE9 (FIGS. 3 and 4). The amplification conditions were 94° C. 3 min, 30 cycles of 94° C. 30 sec, 65° C. 20 sec and 68° C. 3 min, followed by a final extension at 68° C. for 10 min. Amplified fragments were separated by agarose gel electrophoresis, isolated, cloned and analysed by DNA sequencing.

RT-PCR

First strand cDNA, used as a template in the RT-PCR reactions, was synthesised from 1.0 µg total RNA isolated from 12-day-old wheat endosperm. The RNA was primed with oligo(dT)$_{12-18}$ and reverse-transcribed in a total volume of 20 µl using Superscript™ II (Gibco-BRL). PCR reactions (25 µl) were performed with a 0.5 µl aliquot of the first-strand cDNA using the Long Expand Template™ PCR System (Boehringer Mannheim) and the primer pair BE65/BE38 (FIGS. 3 and 4). Reactions were initiated by a denaturation step at 94° C. for 3 min, followed by 30 cycles of 94° C. 30 sec, 65° C. 20 sec, 68° C. 2 min 30 sec and a final 10 min extension at 68° C. Amplified fragments were fractionated by agarose gel electrophoresis, isolated, cloned and analysed by DNA sequencing.

Construction of Expression Vectors

Assembly of the pQE-SBEIc plasmid (FIG. 6A) was initiated by PCR amplification (30 cycles of 94° C., 65° C. 20 sec, 68° C. 2 min 30 sec) of Sbe1c nucleotides 265–1879, using the BE63/BE39 primer pair (FIG. 4). This reaction introduced a NcoI recognition site at the start of the sequence encoding the mature SBEIc. Thereafter, the NcoI—NcoI fragment carrying Sbe1c nucleotides 265–1732 was isolated from the amplified product, filled-in and inserted into a filled-in BamHI site of the His-tag expression vector pQE30 (Qiagen). Construction of pQE-SBEIc was completed by insertion of a 2.2 kb EcoRV-XhoI fragment (Sbe1c nucleotides 1623 to 4563 with XhoI site added at the end) into the EcoRV and SalI sites.

Construct pREP4-cm, encoding the Lac repressor, was derived from pREP4 (Qiagen) by replacing the NPTII gene carried on a ClaI-SmaI fragment, with the chloroamphenicol resistance gene isolated as a PvuII-BstBI fragment from the pACYC184 vector.

Construction of pKKABEI, encoding the mature 87 kD wheat SBEI, was initiated by inserting nucleotides 221–923 (NcoI-KpnI fragment) of pABEI cDNA[19] into NcoI-KpnI sites of the bacterial expression vector pKK388-1 (Clontech). Then nucleotides 923–2729, isolated as a KpnI fragment, were introduced to give pKKABEI. The SBEII expression vector, pQRN33, encoding the mature wheat SBEII was obtained by two cloning steps. First the pRN33[60] nucleotides 317–1442 carried by a HaeIII fragment were inserted into a filled-in BamHI site of the His-tag expression vector pQE31 (Qiagen). The resulting construct was restricted with KpnI and SmaI, followed by introduction of nucleotides 1245–2632 located on a KpnI-PvuII fragment, to give pQRN33.

Analysis of BE Activity Produced in *Escherichia coli*

The BE-deficient *Escherichia coli* strain KV832[23] carrying pREP4-cm was transformed with pQE-SBEIc or the cloning vector pQE30. Plasmids pREP4-cm and pQE30 were also introduced into the BE-positive *Escherichia coli* strain DH5α. The bacterial cultures were grown at 37° C., in liquid YT medium[61] containing 1.0% glucose, 100 µg/ml carbenicillin and 25 µg/ml chloramphenicol, to an $OD_{600}$=0.6, and induced for two hours by addition of IPTG to 1 mM final concentration. Production of SBEIc was verified by SDS-PAGE gel analysis of cell lysates prepared from non-induced and induced cultures.

Visualisation of BE activity in bacterial cells grown on solid media was done by iodine staining of colonies as described by Kossman et al. (1991)[24]. The BE activity levels in cells from non-induced cultures was determined by the phosphorylase a stimulation assay[20] performed at 30° C. for 30 min using two and five µg of soluble protein extract. The cell extracts were prepared from cells of 1 ml culture that were lysed by sonication in 0.25 ml extraction buffer (50 mM Tris-HCl pH 7.5, 2 mM EDTA, 5 mM DTT, 1 mM phenylmethylsulfonyl fluoride) and centrifuged at 15,000×g for 20 min. Determination of protein concentration in the soluble extracts was done using the dye-binding assay (Bio-Rad).

Large Scale Production of Wheat SBE in *Escherichia coli*

A culture of KV832 cells transformed with pKKABEI was grown at 37° C. in LB medium containing 100 µg mL$^{-1}$ ampicillin. At $OD_{600}$=0.6, IPTG was added to a final concentration of 0.5 mM and the culture was grown at 25° C. for 14 h. Cells were harvested by centrifugation and SBEI was purified according to Guan et al. (1994)[63]. The final protein extract was loaded onto a 10% preparative SDS-PAGE gel and the 87 kD SBEI band was isolated by electroelution (Model 422 Electro-eluter™, Bio-Rad). The protein eluate was concentrated using a Centriplus-30™ column (Amicon) before immunisation.

The SBEII expression vector, pQRN33, was introduced into the *Escherichia coli* strain, M15, carrying pREP4 and grown at 22° C. in medium containing 25 g/l tryptone, 15 g/l yeast extract, 5 g/l NaCl, 1% glucose, 100 µg/ml ampicillin and 25 µg/ml kanamycin. Cells were grown to $OD_{600}$=0.7, IPTG was added to give a 1 mM final concentration and the cells were grown for an additional 14 h. Harvested cells were lysed under denaturing conditions and the His-tagged SBEI was purified using the QIAexpress purification system (Qiagen). The guanidine hydrochloride denaturation buffer, column washing buffers and elution buffer were all supplemented with 10 mM β-mercaptoethanol and 0.25% Tween 20. The homogeneity of the column fractions used for immunisation was verified by SDS-PAGE.

Preparation of SBEI and SBEII Antibodies

About 100 µg purified SBEI, or 250 µg His-tagged SBEII in 500 µl phosphate-buffered saline, was emulsified with an equal volume of Freund's complete adjuvant (Difco) and injected intradermally into cereal-starved rabbits. The injection was repeated twice at two-weeks intervals using about 50 µg antigen and an equal volume of Freund's incomplete adjuvant (Difco). The antiserum was collected two weeks after the final injection.

Isolation of Total Starch

Starch granules were extracted from mature and developing wheat kernels according to procedure described by Zhao and Sharp (1996)[64], with the exception of the steeping step, which was only done with mature seeds.

Isolation of A-Type and B-Type Starch Granules

Starch granules were isolated from mature endosperm of five hexaploid wheat cultivars (*Triticum aestivum* L. cv. CDC Teal, McKenzie, AC Karma, AC Crystal, and Fielder), one tetraploid wheat (*Triticum turgidum* L. cv. Plenty) cultivar, barley (*Hordeum vulgare* L.), rye (*Secale cereale* L.), triticale (X *Triticosecale* Wittmack), rice (*Oryza sativa* L.), maize (*Zea mays* L.), canary seed (*Phalaris canariensis* L.) and potato (*Solanum tuberosum* L.) tubers as described by Peng et al. (1999)[27]. Pericarp and developing endosperm tissues were manually dissected from wheat (*Triticum aestivum* L. cv. CDC Teal) kernels and immediately placed in extraction buffer B [50 mM Tris-HCl, pH 7.5, 10 mM EDTA, 5 mM DTT, 10% glycerol, 0.1% (w/v) polyvinyl pyrrolidone] held at 40° C. The pericarp fraction was washed three times with extraction buffer B to remove endosperm starch granules. The endosperm and pericarp fractions were homogenised with a mortar and pestle in three volumes of extraction buffer B and filtered through four layers of Miracloth™ (Calbiochem) to remove cell debris. The crude starch granule fraction was pelleted by centrifugation at 15,000×g for 30 min and further purified as described[27]. The endosperm starch granules were separated into large-size (diameter >10 µm) and small-size (diameter <10 µm) fractions and studied by image analysis as described[27].

Preparation of Endosperm Soluble Fractions

The supernatant remaining from centrifugation of the homogenised endosperm (see above) constituted the endosperm soluble fraction. Protein concentration in the extract was determined using a dye-binding assay from Bio-Rad. For each endosperm fraction, the total amount of extracted soluble protein was determined.

SDS-PAGE Analysis of Starch Granules

Extracted total starch (10 mg) was resuspended in 150 µl of sample buffer (62.5 mM Tris-HCl pH 8.0, 10% SDS, 10% glycerol, 5% β-mercaptoethanol and 0.005% bromophenol blue), boiled for 7 min, cooled on ice for 5 min and centrifuged at 15,000×g for 20 min. Extracted A-type and B-type starch granules (50 mg) were suspended in 350 µl extraction buffer A [62.5 mM Tris-HCl, pH 6.8, 10% (w/v) SDS, 5% (v/v) β-mercaptoethanol], boiled for 15 min, cooled to room temperature, and centrifuged at 15,000×g for 20 min. SDS-PAGE analysis of total and size fractionated starch granules was done on 10% resolving gels (30:0.135) and proteins were visualized by Coomassie blue staining and/or silver staining (BIO-RAD).

Immunoblotting

Total starch granule proteins separated by SDS-PAGE were transferred by vertical electroblotting[61] onto Immobilon™ nitrocellulose membranes (Millipore) at 1.4 V/cm for 2.5 h using buffer 3 described by Bolt and Mahoney (1997)[65]. The filters were blocked for 2 h in blocking buffer

[5% w/v non-fat dry milk, 0.1% Tween 20 in phosphate-buffered saline[61]] and subsequently incubated for 1 h with primary antibodies in blocking buffer (1:1000 dilution). Blots were washed for 1 h in blocking buffer, followed by incubation with alkaline phosphatase-conjugated goat anti-rabbit antibodies (Stratagene) in blocking buffer (1:5000 dilution). Thereafter, the membranes were washed with blocking buffer for 1 h and with 50 mM Tris-HCl pH 7.5, 150 mM NaCl for 45 min. Gel-separated proteins extracted from A-type and B-type granules were electrophoretically transferred at 40° C. onto PVDF membranes (Millipore) using transfer buffer [25 mM Tris-HCl, pH 8.3, 192 mM Glycine and 20% methanol]. Membranes were incubated, for 1 h in TBS buffer [20 mM Tris-HCl, pH 7.5, 150 mM NaCl] containing 3% (w/v) bovine serum albumin, to block nonspecific binding sites. Antibodies, at a dilution of 1:4000 in TBS buffer, were then added to the blot and incubated for 4 h at room temperature. Following three washes in TBS buffer containing 0.05% Tween™ 20 and one wash in TBS buffer, membranes were incubated with alkaline phosphatase-conjugated goat anti-rabbit IgG (Stratagene) at a dilution of 1:5000 for 1 h. Membranes were washed three times in TBS buffer containing 0.05% Tween 20, once in TBS buffer, and equilibrated in 20 mM Tris-HCl, pH 9.5, 100 mM NaCl, 5 mM MgCl2. Immunoreactive bands were detected with 4-nitroblue tetrazolium chloride and 5-bromo-4-chloro-3-indolyl phosphate (Stratagene).

N-Terminal Sequencing of SGP-140 and SGP-145

SGP were extracted from 10 g A-type starch granules of CDC Teal and resolved on preparative SDS-PAGE gels. The migration of SGP-140 and SGP-145 was determined by silver staining a slice of the gel. The proteins were eluted from the unstained part of the gel using an electro-eluter (Model 422 Electro-Eluter™, BIO-RAD) and elution buffer (25 mM Tris, 192 mM glycine, 0.1% SDS). The eluate was dialysed for 8 h against 2 l of dialysis buffer (50 mM Tris-acetate, pH 6.8, 5 mM DTT), with one buffer change. The dialysed solution was concentrated to 500 µl through ultrafiltration (Amicon 100), and 200 µl of the concentrate was loaded on a preparative SDS-PAGE gel. Gel-separated proteins were blotted on a PVDF membrane, as described above. SGP-140 and SGP-145 were identified by amido black staining and subjected to N-terminal sequencing using a gas-phase protein sequencer (Applied Biosystem Model 476A).

Nucleotide and Amino Acid Sequences

SEQ ID NO: 1 is the DNA sequence of Sbe1c
SEQ ID NO: 2 is the amino acid sequence of SBEIc References (incorporated herein by reference)

[1] French D (1984) Organization of Starch Granules. R Whistler, J BeMiller, E Paschall, eds, Starch Chemistry and Technology, Ed 2. Academic Press, New York, pp. 184–242

[2] Evers A D (1973) The size distribution among starch granules in wheat endosperm. Starch/Stärke 25: 303–304

[3] Seib P A (1994) Wheat starch: isolation, structure and properties. Oyo Toshitsu Kagaku 41: 49–69

[4] Parker M L (1985) The relationship between A-type and B-type starch granules in the developing endosperm of wheat. J Cereal Sci 3: 271–278

[5] Ball S, Guan H-P, James M, Myers A, Keeling P, Mouille G, Buleons A, Colonna P, Preiss J (1996) From glycogen to amylopectin: A model for the biogenesis of the plant starch granule. Cell 86: 349–352

[6] Tyynelä J, Schulman A H (1993) An analysis of soluble starch synthase isozymes from the developing grains of normal and shx cv. Bomi barley (Hordeum vulgare). Physiol Plant 89: 835–841

[7] Schulman A H, Tester R F, Ahokas H, Morrison W R (1994) The effect of the shrunken endosperm mutation shx on starch granule development in barley seeds. J Cereal Sci 19: 49–55

[8] Dengate H, Meredith P (1984) Variation in size and distribution of starch granules from wheat grain. J Cereal Sci 2: 83–90

[9] Morrison W R (1989) Uniqueness of wheat starch. Y Pomeranz, ed, Wheat is Unique. American Association of Cereal Chemists, St. Paul, Minn., pp. 193–214

[10] Burton R A, Bewley J D, Smith A M, Bhattacharyya M K, Tatge H, Ring S, Bull V, Hamilton W D O, Martin C (1995) Starch branching enzymes belonging to distinct enzyme families are differentially expressed during pea embryo development. Plant J 7: 3–15

[11] Svensson B (1994) Protein engineering in the α-amylase family: catalytic mechanism, substrate specificity, and stability. Plant Mol Biol 25: 141–157

[12] Bhattacharyya M K, Smith A M, Ellis T H N, Hedley C, Martin C (1990) The wrinkled-seed character of pea described by Mendel is caused by a transposon-like insertion in a gene encoding starch-branching enzyme. Cell 60: 115–122

[13] Smith A M (1988) Major differences in isoforms of starch-branching enzyme between developing embryos of round- and wrinkled-seeded peas (Pisum sativum L.). Planta 175: 270–279

[14] Guan H P, Preiss J (1993) Differentiation of the properties of the branching isozymes from maize (Zea mays). Plant Physiol 102: 1269–1273

[15] Takeda Y, Guan H-P, Preiss J (1993) Branching of amylose by the branching isoenzymes of maize endosperm. Carbohydr Res 240: 253–263

[16] Takeda C, Takeda Y, Hizukuri S (1993) Structure of the amylopectin fraction of amylomaize. Carbohydr Res 246: 273–281

[17] Bäga, M, Glaze S, Mallard C S, Chibbar R N (1999) A starch branching enzyme gene in wheat produces alternatively spliced transcripts. Plant Mol Biol 40: 1019–1030

[18] Rahman S, Abrahams S, Abbott D, Mukai Y, Samuel M, Morell M, Appels R (1997) A complex arrangement of genes at a starch branching enzyme I locus in the D-genome donor of wheat. Genome 40: 465–474

[19] Repellin A, Nair R B, Bäga M, Chibbar R N (1997) Isolation of a starch branching enzyme I cDNA from a wheat endosperm library (Accession No. Y12320) (PGR97-094) Plant Physiol 114: 1135

[20] Hawker J S, Ozbun J L, Ozaki H, Greenberg E, Preiss J (1974) Interaction of spinach leaf adenosine diphosphate glucose α-1,4-glucan α-4-glucosyl transferase and α-1,4-glucan, α-1,4-glucan-6-glycosyl transferase in synthesis of branched α-glucan. Arch Biochem Biophys 160: 530–551

[21] Nakamura T, Vrinten P, Hayakawa K, Ikeda J (1998) Characterisation of a granule-bound starch synthase isoform found in the pericarp of wheat. Plant Physiol 118: 451–459

[22] Gavel Y, von Heijne G (1990) A conserved cleavage-site motif in chloroplast transit peptides. FEBS Lett 261: 455–458

[23] Kiel J A K W, Vossen J P M J, Venema G (1987) A general method for the construction of Escherichia coli

[24] Kossmann J, Visser R G F, Müller-Röber B, Willmitzer L, Sonnewald U (1991) Cloning and expression analysis of a potato cDNA that encodes branching enzyme: evidence for co-expression of starch biosynthetic genes. Mol Gen Genet 230: 39–44 mutants by homologous recombination and plasmid segregation. Mol Gen Genet 207: 294–301

[25] Schofield J D, Greenwell P (1987) Wheat starch granule proteins and their technological significance. I.D. Morton, ed, Cereals in a European context. Ellis Horwood, Chichester, pp 407–420

[26] Rahman S, Kosar-Hashemi B, Samuel M S, Hill A, Abbott D C, Skerritt J H, Preiss J, Appels R, Morell M K (1995) The major proteins of wheat endosperm starch granules. Aust J Plant Physiol 22: 793–803

[27] Peng M, Gao M, Abdel-Aal E S, Hucl P, Chibbar R N (1999) Separation and characterisation of A- and B-type starch granules in wheat endosperm. Cereal Chem 76: 375–379

[29] Sulaiman B D, Morrison W R (1990) Proteins associated with the surface of wheat starch granules purified by centrifuging through cesium chloride. J Cereal Sci 12: 53–61

[30] Briarty L G, Hughes C E, Evers A D (1979) The developing endosperm of wheat—a stereological analysis. Ann Bot 44: 641–658

[31] Morrison W R, Gadan H (1987) The amylose and lipid contents of starch granules in developing wheat endosperm. J Cereal Sci 5: 263–275

[32] Slattery C J, Kavakli I H, Okita T W (2000) Engineering starch for increased quantity and quality. Trends Plant Sci 5: 291–298

[33] Ellis R P, Cochrane M P, Dale M F B, Duffus C M, Lynn A, Morrison I M, Prentice R D M, Swanston J S, Tiller S A (1998) Starch production and industrial use. J Sci Food Agric 77: 289–311.

[34] Nachtergaele W, Van Nuffel J (1989) Starch as stilt material in carbonless copy paper-New developments. Starch/Staerke 41: 386–392.

[35] Iyer L M, Kumpatla S P, Chandrasekharan M B, Hall T C (2000) Transgene silencing in monocots. Plant Mol Biol 43: 323–346.

[36] Baulcombe D C (1996) RNA as a target and an initiator of post-transcriptional gene silencing in transgenic plants. Plant Mol Biol 32: 79–88.

[37] Vaucheret H, Beclin C, Elmayan T, Feuerbach F, Godon C, Morel J-B, Mourrain P, Palauqui J-C, Vernhettes S (1998) Transgene-induced gene silencing in plants. Plant J 16: 651–659.

[38] Higgins D G, Sharp P M (1988) CLUSTAL: a package for performing multiple sequence alignment on a microcomputer. GENE 73: 237–244

[39] Jane J, Shen L, Wang L, Maningat C C (1992) Preparation and properties of small-particle corn starch. Cereal Chem 69: 280–283.

[40] Lim S, Jane J, Rajagopalan S, Seib P A (1992) Effect of starch granule size on physical properties of starch-filled polyethylene film. Biotechnol Prog 8: 51–57

[41] Mountain A, Ney U, Schomburg D (1999) Biotechnology: A Multi-Volume Comprehensive Treatise, Volume 5A, Recombinant Proteins, Monoclonal Antibodies, and Therapeutic Genes, 2nd Completely Revised Edition. Wiley-Interscience, UK

[42] Delves P J (1995) Antibody Applications: Essential Techniques, Wiley-Interscience, UK

[43] Liddell J E, Cryer A (1991) A Practical Guide to Monoclonal Antibodies, Wiley-Interscience, UK

[44] Birch J R, Lennox, E S (1995) Monoclonal Antibodies: Principles and Applications, Wiley-Interscience, UK

[45] Potrykus I (1991) Gene transfer to plants: Assessment of published approaches and results. Ann Rev Plant Physiol Plant Mol Biol 42: 205–225.

[46] Vasil I K (1994) Molecular improvement of cereals. Plant Mol Biol 25: 925–937.

[47] Walden R, Wingender R (1995) Gene-transfer and plant regeneration techniques. Trends Biotechnol 13: 324–331.

[48] Songstad D D, Somers D A, Griesbach R J (1995) Advances in alternative DNA delivery techniques. Plant CellTiss OrgCult 40: 1–15.

[49] Bechtold N, Ellis J, Pelletier G (1993) In planta *Agrobacterium*-mediated gene transfer by infiltration of adult *Arabidopsis thaliana* plants. C R Acad Sci Paris, Sciences de la vie/Life sciences 316: 1194–1199.

[50] Katavic V, Haughn G W, Reed D, Martin M, Kunst L (1994) In planta transformation of *Arabidopsis thaliana*. Mol Gen Genet 245: 363–370.

[51] De Block M, De Brouwer D, Tenning P (1989) Transformation of *Brassica napus* and *Brassica oleracea* using *Agrobacterium tumefaciens* and the expression of the bar and neo genes in the transgenic plants. Plant Physiol 91: 694–701.

[52] Moloney M M, Walker J M, Sharma K K (1989) High efficiency transformation of *Brassica napus* using *Agrobacterium* vectors. Plant Cell Rep 8: 238–242.

[53] Sanford J C, Klein T M, Wolf E D, Allen N (1987) Delivery of substances into cells and tissues using a particle bombardment process. J Part Sci Technol 5: 27–37.

[54] Nehra N S, Chibbar R N, Leung N, Caswell K, Mallard C, Steinhauer L, Baga M, Kartha K K (1994) Self-fertile transgenic wheat plants regenerated from isolated scutellar tissues following microprojectile bombardment with two distinct gene constructs. Plant J. 5: 285–297.

[55] Becker D, Brettschneider R, Lörz H (1994) Fertile transgenic wheat from microprojectile bombardment of scutellar tissue. Plant J 5: 299–307.

[56] Rhodes C A, Pierce D A, Mettler I J, Mascarenhas D, Detmer J J (1988) Genetically transformed maize plants from protoplasts. Science 240: 204–207.

[57] Shimamoto K, Terada R, Izawa T, Fujimoto H (1989) Fertile transgenic rice plants regenerated from transformed protoplasts. Nature 338: 274–276.

[58] Meyer P (1995) Understanding and controlling transgene expression. Trends Biotechnol 13: 332–337.

[59] Datla R, Anderson J W, Selvaraj G (1997) Plant promoters for transgene expression. Biotech Ann Rev 3: 269–296.

[60] Nair R B, Bäga M, Scoles G J, Kartha K K, Chibbar R N (1997) Isolation, characterisation and expression analysis of a starch branching enzyme II cDNA from wheat. Plant Sci 122: 153–163

[61] Sambrook J, Fritsch E F, Maniatis T (1989) Molecular cloning: A laboratory manual, Ed 2. Cold Spring Harbor Laboratory Press, Cold Spring Harbor, N.Y.

[62] Bäga M, Chibbar R N, Kartha K K (1995) Molecular cloning and expression analysis of peroxidase genes from wheat. Plant Mol Biol 29: 647–662

[63] Guan H P, Baba T, Preiss J (1994) Expression of branching enzyme I of maize endosperm in *Escherichia coli*. Plant Physiol 104: 1449–1453

[64] Zhao X C, Sharp P J (1996) An improved 1-D SDS-PAGE method for the identification of three bread wheat 'waxy' proteins. J Cereal Sci 23: 191–193

[65] Bolt M W, Mahoney P A (1997) High-efficiency blotting of proteins of diverse sizes following sodium dodecyl sulfate-polyacrylamide gel electrophoresis. Anal Biochem 247: 185–192

SEQUENCE LISTING

<160> NUMBER OF SEQ ID NOS: 2

<210> SEQ ID NO 1
<211> LENGTH: 4563
<212> TYPE: DNA
<213> ORGANISM: Triticum aestivum

<400> SEQUENCE: 1

```
gggactttcg tccgccacca aggctgacag ctccaccgcc ctcggttgcg ccgtcgacga     60
cgatgctttg cctcagctcc tctctcctgc cgcgcccgtc tgccgctgct gaccggccgg    120
ctcccgggat catcgcgggc ggcggcggca agcggctgag cgtggtgccg gctgtcccgt    180
ttttacttcg ctggtcgtgg ccacggaagg ccaagagcag gtcttctgtt tccgtgactg    240
cacgaggaaa caaaattgcg gcagcaaatg gatatggttc tgaccacctt cccatgtatg    300
atctggaacc aaagttggct gaattcaaag accacttcaa ctatacgatg aaaaggtacc    360
ttgaacagaa acttttgatt gagaaacatg agggaggcct agaggaattc tctaaaggct    420
atttgaagtt tgggatcaac acggagcatg gtgcatctct gtacagggaa tgggcccctg    480
cagcagagga agcacaacta gttggtgact tcaacaactg gaatggttct ggccacaaga    540
tgacgaagga taactttggc gtttggtcaa tcaggatttc ccatgtcaat gggaaacctg    600
ccatccctca caattccaag gttaaatttc gatttaggca tgatggagta tgggttgaac    660
ggattccagc atggattcgt tatgcaactg ttactgcctc tgaatctgga gctccatatg    720
atggtgttca ctgggatcca ccaactagtg aaaggtatgt atttaaccat cctcgacctc    780
caaagcctga tgttccacgt atctatgagg ctcatgtggg ggtgagtggt ggaaagcttg    840
aagcaggcac acacagggaa tttgcagaca atgtgttacc gcgcttaagg gcaactacat    900
acaacacggt tcagttgatg ggaatcatgg aacattctga cgctgcttct tttgggtatt    960
atgtgacgaa tttcttcgca gttagcagca gatcaggcac accagacgac ctcaaatatc   1020
ttattgacaa ggcacatagt cttggattgt gtgttctgat ggatgttgtc cacagccatg   1080
cgagcaataa tgtgatagat ggtcccaatg gctatgatgt tggacaaagt gcacacgaat   1140
cctatttcta cacaggagac agggctata ataagatgtg gaatggccgc atgttcaact   1200
atgccaattg ggaggtccta agattcctgc tttccaattt gagatattgg atggacgaat   1260
tcatgtttga tggcttccga tttgttgggg ttacatcgat gctatataat caaaatggta   1320
tcaatatgtc attcactgga aattacaaag agtattttgg tttggatacc aatgtagatg   1380
cagttgttta tatgatgctc gcgaaccatt aatgcacaa actctaccca gaagcaattg   1440
ttgtggccgt agatgtttca ggcatgccag ttctttgttg gccagttgat gaaggtggat   1500
tagggtttga ctatcgccag gctatgacta ttcccgatag atggattgaa tacttggaga   1560
acaaaggtga tcaacagtgg tcaatgagta gtgtaatatc acaaactttg actaacaggc   1620
gatatccgga aaagttcatt gcgtatgctg agaggcaaaa tcattctatt attggcagca   1680
agactatggc atttctcttg atgggatggg aaacgtattc cggtatgtcg gccatggagc   1740
ctgattcacc tacaatagat cgtggcattg cacttcaaaa gatgattcat ttcatcagga   1800
tggccttttgg aggtgatagc tacttaaaat ttatgggtaa tgagtacatg aatgcatttg   1860
```

```
atcaagcagt ggacacgccc agcgataaat gttccttcct atcatcatca aagcagactg    1920
ccagcgacat gaatgaggaa gaaaaggcca agagcaagtt ctctgttccc gtgtctgcgc    1980
caagagacta caccatggca acagctgaag atggtgttgg cgaccttccg atatacgatc    2040
tggatccgaa gtttgccggc ttcaaggaac acttcagtta taggatgaaa agtaccttg     2100 accagaaaca ttcgattgag aagcacgagg gaggccttga agagttctct aaaggctatt    2160
tgaagtttgg gatcaacaca gaaaatgacg caactgtgta ccgggaatgg gcccctgcag    2220
caatggatgc acaacttatt ggtgacttca acaactggaa tggctctggg cacaggatga    2280
caaaggataa ttatggtgtt tggtcaatca ggatttccca tgtcaatggg aaacctgcca    2340
tcccccataa ttccaaggtt aaatttcgat tcaccgtgg agatggacta tgggtcgatc     2400
gggttcctgc atggattcgt tatgcaactt tgatgcctc taaatttgga gctccatatg     2460
acggtgttca ctgggatcca ccttctggtg aaaggtatgt gtttaagcat cctcggcctc    2520
gaaagcctga cgctccacgt atttacgagg ctcatgtggg gatgagtggt gaaaagcctg    2580
aagtaagcac atacagagaa tttgcagaca atgtgttacc gcgcataaag gcaaacaact    2640
acaacacagt tcagctgatg gcaatcatgg aacattcata ttatgcttct tttgggtacc    2700
atgtgacgaa tttcttcgca gttagcagca gatcaggaac gccagaggac ctcaaatatc    2760
ttgttgacaa ggcacatagt ttagggttgc gtgttctgat ggatgttgtc catagccatg    2820
cgagcagtaa taagacagat ggtcttaatg ctatgatgt tgggcaaaac acacaggagt     2880
cctatttcca cacaggagaa aggggctatc ataaactgtg ggatagccgc ctgttcaact    2940
atgccaattg ggaggtctta cgatttcttc tttctaatct gagatattgg atggacgaat    3000
tcatgtttga tggcttccga tttgatgggg taacatccat gctatataat caccatggta    3060
tcaatatgtc attcgctgga agttacaagg aatattttgg tttggatact gatgtagatg    3120
cagttgttta cctgatgctt gcgaaccatt taatgcacaa actcttgcca gaagcaactg    3180
ttgttgcaga agatgtttca ggcatgccag tgctttgtcg gtcagttgat gaaggtggag    3240
tagggtttga ctatcgcctg gctatggcta ttcctgatag atggatcgac tacttgaaga    3300
acaaagatga ccttgaatgg tcaatgagtg gaatagcaca tactctgacc aacaggagat    3360
atacggaaaa gtgcattgca tatgctgaga gccatgatca gtctattgtt ggcgacaaga    3420
ctatggcatt tctcttgatg gacaaggaaa tgtatactgg catgtcagac ttgcagcctg    3480
cttcgcctac aattgatcgt ggaattgcac ttcaaaagat gattcacttc atcaccatgg    3540
cccttggagg tgatggctac ttgaattttat gggtaatga gtttggccac ccagaatgga    3600
ttgactttcc aagagaaggc aacaactgga gttatgataa atgcagacgc cagtggagcc    3660
tcgcagacat tgatcaccta cgatacaagt acatgaacgc atttgatcaa gcaatgaatg    3720
cgctcgacga caaatttttcc ttcctatcat catcaaagca gattgtcagc gacatgaatg    3780
aggaaaagaa gattattgta tttgaacgtg gagatctggt cttcgtcttc aattttcatc    3840 ccagtaaaaac ttatgatggt tacaaagtcg gatgtgactt gcctgggaag tacaaggtag    3900
ctctggactc tgatgctctg atgtttggtg acatggaag agtggcccat gacaacgatc      3960
actttacgtc acctgaagga gtaccaggag tacctgaaac aaacttcaac aaccgccctaa    4020 actcattcaa aatcctgtct ccatcccgca cttgtgtggc ttactatcgc gtcgaggaga    4080
aagcggaaaa gcccaaggat gaaggagctg cttcttgggg gaaaactgct ctcgggtaca    4140
tcgatgttga agccactggc gtcaaagacg cagcagatgg tgaggcgact tctggttccg    4200
```

-continued

```
aaaaggcgtc tacaggaggt gactccagca agaagggaat taactttgtc tttctgtcac    4260
ccgacaaaga caacaaataa gcaccatatc aacgcttgat caggaccgtg tgccgacgtc    4320
cttgtaatac tcctgctatt gctagtagta gcaatactgt caaactgtgc agacttgaga    4380
ttctggcttg gactttgctg aggttaccta ctatatagaa agataaataa gcggtgatgg    4440
tgcgggtcga gtccagctat atgtgccaaa tatgcgccat cccgagtcct ctgtcataaa    4500
gaaagtttcg ggcttccatc ccagaataaa aacagttgtc tgtttgccca aaaaaaaaaa    4560
aaa                                                                  4563
```

<210> SEQ ID NO 2
<211> LENGTH: 1405
<212> TYPE: PRT
<213> ORGANISM: Triticum aestivum

<400> SEQUENCE: 2

```
Met Leu Cys Leu Ser Ser Leu Leu Pro Arg Pro Ser Ala Ala Ala
  1               5                  10                  15

Asp Arg Pro Ala Pro Gly Ile Ile Ala Gly Gly Gly Lys Arg Leu
                 20                  25                  30

Ser Val Val Pro Ala Val Pro Phe Leu Leu Arg Trp Ser Trp Pro Arg
         35                      40                  45

Lys Ala Lys Ser Arg Ser Val Ser Val Thr Ala Arg Gly Asn Lys
     50                      55                  60

Ile Ala Ala Ala Asn Gly Tyr Gly Ser Asp His Leu Pro Met Tyr Asp
 65                  70                  75                  80

Leu Glu Pro Lys Leu Ala Glu Phe Lys Asp His Phe Asn Tyr Thr Met
                 85                  90                  95

Lys Arg Tyr Leu Glu Gln Lys Leu Leu Ile Glu Lys His Glu Gly Gly
                100                 105                 110

Leu Glu Glu Phe Ser Lys Gly Tyr Leu Lys Phe Gly Ile Asn Thr Glu
            115                 120                 125

His Gly Ala Ser Leu Tyr Arg Glu Trp Ala Pro Ala Ala Glu Glu Ala
    130                 135                 140

Gln Leu Val Gly Asp Phe Asn Asn Trp Asn Gly Ser Gly His Lys Met
145                 150                 155                 160

Thr Lys Asp Asn Phe Gly Val Trp Ser Ile Arg Ile Ser His Val Asn
                165                 170                 175

Gly Lys Pro Ala Ile Pro His Asn Ser Lys Val Lys Phe Arg Phe Arg
                180                 185                 190

His Asp Gly Val Trp Val Glu Arg Ile Pro Ala Trp Ile Arg Tyr Ala
            195                 200                 205

Thr Val Thr Ala Ser Glu Ser Gly Ala Pro Tyr Asp Gly Val His Trp
    210                 215                 220

Asp Pro Pro Thr Ser Glu Arg Tyr Val Phe Asn His Pro Arg Pro Pro
225                 230                 235                 240

Lys Pro Asp Val Pro Arg Ile Tyr Glu Ala His Val Gly Val Ser Gly
                245                 250                 255

Gly Lys Leu Glu Ala Gly Thr His Arg Glu Phe Ala Asp Asn Val Leu
            260                 265                 270

Pro Arg Leu Arg Ala Thr Thr Tyr Asn Thr Val Gln Leu Met Gly Ile
        275                 280                 285

Met Glu His Ser Asp Ala Ala Ser Phe Gly Tyr Tyr Val Thr Asn Phe
    290                 295                 300
```

```
Phe Ala Val Ser Ser Arg Ser Gly Thr Pro Asp Asp Leu Lys Tyr Leu
305                 310                 315                 320

Ile Asp Lys Ala His Ser Leu Gly Leu Cys Val Leu Met Asp Val Val
            325                 330                 335

His Ser His Ala Ser Asn Asn Val Ile Asp Gly Pro Asn Gly Tyr Asp
            340                 345                 350

Val Gly Gln Ser Ala His Glu Ser Tyr Phe Tyr Thr Gly Asp Arg Gly
        355                 360                 365

Tyr Asn Lys Met Trp Asn Gly Arg Met Phe Asn Tyr Ala Asn Trp Glu
    370                 375                 380

Val Leu Arg Phe Leu Leu Ser Asn Leu Arg Tyr Trp Met Asp Glu Phe
385                 390                 395                 400

Met Phe Asp Gly Phe Arg Phe Val Gly Val Thr Ser Met Leu Tyr Asn
                405                 410                 415

Gln Asn Gly Ile Asn Met Ser Phe Thr Gly Asn Tyr Lys Glu Tyr Phe
            420                 425                 430

Gly Leu Asp Thr Asn Val Asp Ala Val Val Tyr Met Met Leu Ala Asn
        435                 440                 445

His Leu Met His Lys Leu Tyr Pro Glu Ala Ile Val Val Ala Val Asp
    450                 455                 460

Val Ser Gly Met Pro Val Leu Cys Trp Pro Val Asp Glu Gly Gly Leu
465                 470                 475                 480

Gly Phe Asp Tyr Arg Gln Ala Met Thr Ile Pro Asp Arg Trp Ile Glu
                485                 490                 495

Tyr Leu Glu Asn Lys Gly Asp Gln Gln Trp Ser Met Ser Ser Val Ile
            500                 505                 510

Ser Gln Thr Leu Thr Asn Arg Arg Tyr Pro Glu Lys Phe Ile Ala Tyr
        515                 520                 525

Ala Glu Arg Gln Asn His Ser Ile Ile Gly Ser Lys Thr Met Ala Phe
    530                 535                 540

Leu Leu Met Gly Trp Glu Thr Tyr Ser Gly Met Ser Ala Met Glu Pro
545                 550                 555                 560

Asp Ser Pro Thr Ile Asp Arg Gly Ile Ala Leu Gln Lys Met Ile His
                565                 570                 575

Phe Ile Arg Met Ala Phe Gly Gly Asp Ser Tyr Leu Lys Phe Met Gly
            580                 585                 590

Asn Glu Tyr Met Asn Ala Phe Asp Gln Ala Val Asp Thr Pro Ser Asp
        595                 600                 605

Lys Cys Ser Phe Leu Ser Ser Lys Gln Thr Ala Ser Asp Met Asn
    610                 615                 620

Glu Glu Glu Lys Ala Lys Ser Lys Phe Ser Val Pro Val Ser Ala Pro
625                 630                 635                 640

Arg Asp Tyr Thr Met Ala Thr Ala Glu Asp Gly Val Gly Asp Leu Pro
                645                 650                 655

Ile Tyr Asp Leu Asp Pro Lys Phe Ala Gly Phe Lys Glu His Phe Ser
            660                 665                 670

Tyr Arg Met Lys Lys Tyr Leu Asp Gln Lys His Ser Ile Glu Lys His
        675                 680                 685

Glu Gly Gly Leu Glu Glu Phe Ser Lys Gly Tyr Leu Lys Phe Gly Ile
    690                 695                 700

Asn Thr Glu Asn Asp Ala Thr Val Tyr Arg Glu Trp Ala Pro Ala Ala
705                 710                 715                 720

Met Asp Ala Gln Leu Ile Gly Asp Phe Asn Asn Trp Asn Gly Ser Gly
```

-continued

```
                725                 730                 735
His Arg Met Thr Lys Asp Asn Tyr Gly Val Trp Ser Ile Arg Ile Ser
            740                 745                 750
His Val Asn Gly Lys Pro Ala Ile Pro His Asn Ser Lys Val Lys Phe
        755                 760                 765
Arg Phe His Arg Gly Asp Gly Leu Trp Val Asp Arg Val Pro Ala Trp
    770                 775                 780
Ile Arg Tyr Ala Thr Phe Asp Ala Ser Lys Phe Gly Ala Pro Tyr Asp
785                 790                 795                 800
Gly Val His Trp Asp Pro Pro Ser Gly Glu Arg Tyr Val Phe Lys His
                805                 810                 815
Pro Arg Pro Arg Lys Pro Asp Ala Pro Arg Ile Tyr Glu Ala His Val
            820                 825                 830
Gly Met Ser Gly Glu Lys Pro Glu Val Ser Thr Tyr Arg Glu Phe Ala
        835                 840                 845
Asp Asn Val Leu Pro Arg Ile Lys Ala Asn Asn Tyr Asn Thr Val Gln
    850                 855                 860
Leu Met Ala Ile Met Glu His Ser Tyr Tyr Ala Ser Phe Gly Tyr His
865                 870                 875                 880
Val Thr Asn Phe Phe Ala Val Ser Ser Arg Ser Gly Thr Pro Glu Asp
                885                 890                 895
Leu Lys Tyr Leu Val Asp Lys Ala His Ser Leu Gly Leu Arg Val Leu
            900                 905                 910
Met Asp Val Val His Ser His Ala Ser Ser Asn Lys Thr Asp Gly Leu
        915                 920                 925
Asn Gly Tyr Asp Val Gly Gln Asn Thr Gln Glu Ser Tyr Phe His Thr
    930                 935                 940
Gly Glu Arg Gly Tyr His Lys Leu Trp Asp Ser Arg Leu Phe Asn Tyr
945                 950                 955                 960
Ala Asn Trp Glu Val Leu Arg Phe Leu Leu Ser Asn Leu Arg Tyr Trp
                965                 970                 975
Met Asp Glu Phe Met Phe Asp Gly Phe Arg Phe Asp Gly Val Thr Ser
            980                 985                 990
Met Leu Tyr Asn His His Gly Ile Asn Met Ser Phe Ala Gly Ser Tyr
        995                 1000                1005
Lys Glu Tyr Phe Gly Leu Asp Thr Asp Val Asp Ala Val Val Tyr Leu
    1010                1015                1020
Met Leu Ala Asn His Leu Met His Lys Leu Leu Pro Glu Ala Thr Val
1025                1030                1035                1040
Val Ala Glu Asp Val Ser Gly Met Pro Val Leu Cys Arg Ser Val Asp
                1045                1050                1055
Glu Gly Gly Val Gly Phe Asp Tyr Arg Leu Ala Met Ala Ile Pro Asp
            1060                1065                1070
Arg Trp Ile Asp Tyr Leu Lys Asn Lys Asp Asp Leu Glu Trp Ser Met
        1075                1080                1085
Ser Gly Ile Ala His Thr Leu Thr Asn Arg Arg Tyr Thr Glu Lys Cys
    1090                1095                1100
Ile Ala Tyr Ala Glu Ser His Asp Gln Ser Ile Val Gly Asp Lys Thr
1105                1110                1115                1120
Met Ala Phe Leu Leu Met Asp Lys Glu Met Tyr Thr Gly Met Ser Asp
                1125                1130                1135
Leu Gln Pro Ala Ser Pro Thr Ile Asp Arg Gly Ile Ala Leu Gln Lys
            1140                1145                1150
```

```
Met Ile His Phe Ile Thr Met Ala Leu Gly Gly Asp Gly Tyr Leu Asn
    1155                1160                1165

Phe Met Gly Asn Glu Phe Gly His Pro Glu Trp Ile Asp Phe Pro Arg
    1170                1175                1180

Glu Gly Asn Asn Trp Ser Tyr Asp Lys Cys Arg Arg Gln Trp Ser Leu
1185                1190                1195                1200

Ala Asp Ile Asp His Leu Arg Tyr Lys Tyr Met Asn Ala Phe Asp Gln
            1205                1210                1215

Ala Met Asn Ala Leu Asp Asp Lys Phe Ser Phe Leu Ser Ser Ser Lys
            1220                1225                1230

Gln Ile Val Ser Asp Met Asn Glu Glu Lys Lys Ile Ile Val Phe Glu
            1235                1240                1245

Arg Gly Asp Leu Val Phe Val Phe Asn Phe His Pro Ser Lys Thr Tyr
        1250                1255                1260

Asp Gly Tyr Lys Val Gly Cys Asp Leu Pro Gly Lys Tyr Lys Val Ala
1265                1270                1275                1280

Leu Asp Ser Asp Ala Leu Met Phe Gly Gly His Gly Arg Val Ala His
            1285                1290                1295

Asp Asn Asp His Phe Thr Ser Pro Glu Gly Val Pro Gly Val Pro Glu
            1300                1305                1310

Thr Asn Phe Asn Asn Arg Pro Asn Ser Phe Lys Ile Leu Ser Pro Ser
        1315                1320                1325

Arg Thr Cys Val Ala Tyr Tyr Arg Val Glu Glu Lys Ala Glu Lys Pro
    1330                1335                1340

Lys Asp Glu Gly Ala Ala Ser Trp Gly Lys Thr Ala Leu Gly Tyr Ile
1345                1350                1355                1360

Asp Val Glu Ala Thr Gly Val Lys Asp Ala Ala Asp Gly Glu Ala Thr
            1365                1370                1375

Ser Gly Ser Glu Lys Ala Ser Thr Gly Gly Asp Ser Ser Lys Lys Gly
            1380                1385                1390

Ile Asn Phe Val Phe Leu Ser Pro Asp Lys Asp Asn Lys
        1395                1400                1405
```

What is claimed is:

1. An isolated starch branching enzyme characterized in that it is bound to A-type starch granules in wheat, rye, barley or triticale endosperm, said enzyme comprising an amino acid sequence as shown in SEQ ID NO:2.

2. An isolated starch branching enzyme according to claim 1, characterized in that said amino acid sequence is a sequence encoded by the DNA sequence shown in SEQ ID NO:1.

3. A method for modifying starch comprising a step of exposing glucose polymers to a starch branching enzyme that is bound to A-type starch granules in wheat, rye, barley or triticale endosperm, wherein the starch branching enzyme comprises an amino acid sequence as shown in SEQ ID NO:2.

* * * * *